United States Patent
Yaginuma et al.

(10) Patent No.: US 12,270,048 B2
(45) Date of Patent: Apr. 8, 2025

(54) MANUFACTURING METHOD FOR SUBSTRATE ON WHICH NERVE CELLS ARE ARRANGED

(71) Applicant: RICOH COMPANY, LTD., Tokyo (JP)

(72) Inventors: Hidekazu Yaginuma, Kanagawa (JP); Masayuki Yumoto, Kanagawa (JP); Tatsuya Sameshima, Kanagawa (JP); Naoki Satoh, Kanagawa (JP); Natsuko Iwashita, Tokyo (JP); Takahiko Matsumoto, Kanagawa (JP); Yusuke Nonoyama, Kanagawa (JP); Takehiro Yamazaki, Saitama (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 17/189,434

(22) Filed: Mar. 2, 2021

(65) Prior Publication Data

US 2021/0292709 A1   Sep. 23, 2021

(30) Foreign Application Priority Data

Mar. 23, 2020 (JP) ................ 2020-050906
Jul. 3, 2020 (JP) ................ 2020-115635
Dec. 25, 2020 (JP) ................ 2020-217760

(51) Int. Cl.
   *C12N 5/079* (2010.01)
(52) U.S. Cl.
   CPC ........ *C12N 5/0618* (2013.01); *C12N 2500/70* (2013.01); *C12N 2537/00* (2013.01)
(58) Field of Classification Search
   CPC ............. C12N 5/0618; C12N 2500/70; C12N 2537/00
   See application file for complete search history.

(56) References Cited

U.S. PATENT DOCUMENTS 6,027,695 A    2/2000  Oldenburg et al.
11,004,199 B2  5/2021  Mouton et al.
(Continued)

FOREIGN PATENT DOCUMENTS

EP  3540041     9/2019
JP  5607535 B2  10/2014
(Continued)

OTHER PUBLICATIONS

Amruth et al., Inkjet printing technique and its application in organic light emitting diodes, Display and imaging, 2: 339-358. (Year: 2017).*
(Continued)

*Primary Examiner* — Mark L Shibuya
(74) *Attorney, Agent, or Firm* — Grüneberg and Myers PLLC

(57) ABSTRACT

An object of the present invention is to provide a technique for precisely arranging nerve cells on a substrate while suppressing the migration of nerve cells.
A manufacturing method for a substrate on which nerve cells are arranged is provided, the method including a step of arranging, on a substrate, a plurality of liquid droplets containing nerve cells by an inkjet method to form one or a plurality of liquid pools, the substrate having a region in which a cell adhesive material is arranged and a region in which a cell non-adhesive material is arranged; and a step of incubating the liquid pool until the nerve cells sediment and temporarily adhere onto the substrate to form a cell aggregate. The diameter per one liquid pool is 500 μm or less, and the density of nerve cells per one liquid pool is $10^5$ cells/cm$^2$ or more.

19 Claims, 16 Drawing Sheets

(56) References Cited

U.S. PATENT DOCUMENTS

| | | | |
|---|---|---|---|
| 2010/0021866 A1 | 1/2010 | Tsuji et al. | |
| 2010/0279320 A1 | 11/2010 | Huang | |
| 2011/0217725 A1 | 9/2011 | Itchoda et al. | |
| 2013/0330325 A1 | 12/2013 | Grabe et al. | |
| 2014/0227784 A1 | 8/2014 | Ejiri et al. | |
| 2015/0024966 A1 | 1/2015 | Brodie et al. | |
| 2017/0267975 A1 | 9/2017 | Hasegawa et al. | |
| 2019/0284524 A1 | 9/2019 | Yaginuma et al. | |
| 2019/0309257 A1 | 10/2019 | Aratani et al. | |
| 2019/0381500 A1 | 12/2019 | Takagi et al. | |
| 2020/0048602 A1* | 2/2020 | Hickman | C12N 5/0068 |
| 2020/0299638 A1 | 9/2020 | Shionoiri et al. | |

FOREIGN PATENT DOCUMENTS

| | | |
|---|---|---|
| JP | 5666490 B2 | 2/2015 |
| JP | 2015-510401 A | 4/2015 |
| JP | 2019-162097 A | 9/2019 |
| JP | 2019-180394 A | 10/2019 |

OTHER PUBLICATIONS

Ahn et al., Effect of pore architecture on oxygen diffusion in 3D scaffolds for tissue engineering, Journal of Biomedical Engineering, 132: 104506-1-104506-5. (Year: 2010).*

Sanjana et al., A fast flexible ink-jet printing method for patterning dissociated neurons in culture, Journal of neuroscience Methods, 136: 151-163. (Year: 2004).*

Park et al., Freeform micropatterning of living cells into cell culture medium using direct inkjet printing, Scientific Reports, 7: 1-11 (Year: 2017).*

Tse et al., Inkjet printing Schwann cells and neuronal analogue NG108-15 cells, Biofabrication, 8: 1-9. (Year: 2016).*

Sawadkar et al., Three dimensional porous scaffolds derived from collagen, elastin and fibrin proteins orchestrate adipose tissue regeneration, Journal of Tissue Engineering, 12: 1-17. (Year: 2021).*

Kushiro et al., Slope-Dependent Cell Motility Enhancements at the Walls of PEG-Hydrogel Microgroove Structures, Langmuir, 31: 10215-10222. (Year: 2015).*

Saunders et al., Inkjet printing biomaterials for tissue engineering: bioprinting, International Materials Reviews, 59(8): 430-448. (Year: 2014).*

Ooi et al., Thiol-Ene Alginate Hydrogels as Versatile Bioinks for Bioprinting, Biomacromolecules, 19: 3390-3400. (Year: 2018).*

Extended European Search Report issued Aug. 10, 2021 in European Application 21161104.1., 9 pages.

Knowlton, et al., "*Bioprinting for Neural Tissue Engineering*", Trends in Neurosciences, vol. 41, No. 1, Jan. 2018, pp. 31-46.

Lee, et al., "*Three-dimensional bioprinting of rat embryonic neural cells*", NeuroReport, vol. 20, No. 8, 2009, pp. 798-803.

Lorber, et al., "*Adult rat retinal ganglion cells and glia can be printed by piezoelectric inkjet printing*", Biofabrication, 6, 2014, 10 pages.

Xu, et al., "*Viability and electrophysiology of neural cell structures generated by the inkjet printing method*", Biomaterials, vol. 27, 2006, pp. 3580-3588.

U.S. Appl. No. 62/985,904, filed Mar. 6, 2020.

\* cited by examiner

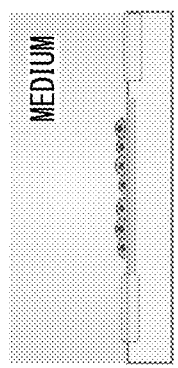
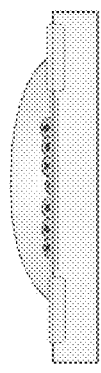
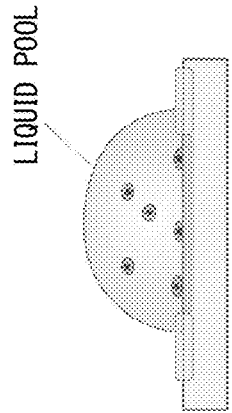
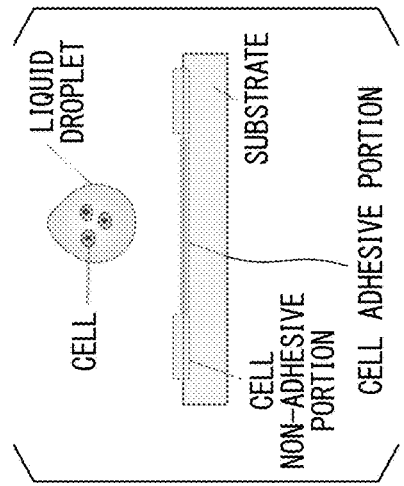
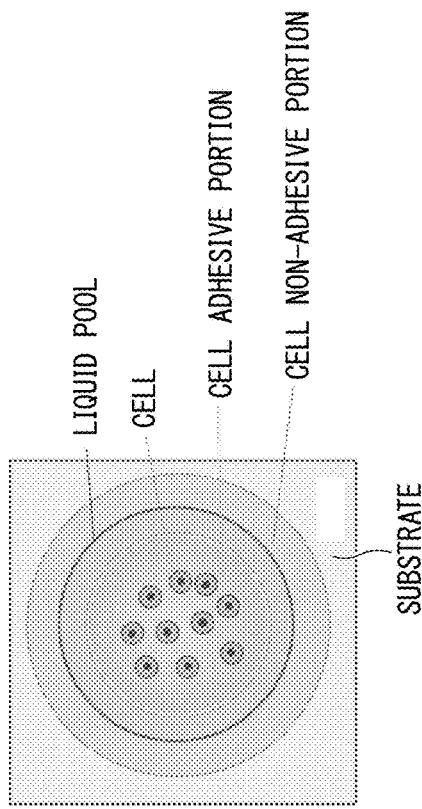
FIG. 15A  FIG. 15B  FIG. 15C  FIG. 15D
FIG. 15E

US 12,270,048 B2

MANUFACTURING METHOD FOR SUBSTRATE ON WHICH NERVE CELLS ARE ARRANGED

BACKGROUND OF THE INVENTION

Field of the Invention

The present invention relates to a manufacturing method for a substrate on which nerve cells are arranged. Priority is claimed on Japanese Patent Application No. 2020-050906 filed in Japan on Mar. 23, 2020, Japanese Patent Application No. 2020-115635 filed in Japan on Jul. 3, 2020, and Japanese Patent Application No. 2020-217760 filed in Japan on Dec. 25, 2020, the content of which are incorporated herein by reference.

Description of Related Art

Nerve cells form a network in the living body and perform their actions in a functionally connected state. In the elucidation of the brain function, the toxicity evaluation of nerve system-involved disease, drug discovery and drug development, or the like, it is necessary to reproduce in vitro the activity state of nerve cells in the living body as accurately as possible, which is considered to be important for enhancing the extrapolation property of test results (the correlation with clinical data).

For this purpose, it is considered effective to develop a neural circuit model in which any nerve cells are arranged at predetermined positions and the nerve cells extend axons and are functionally connected to each other. However, it is difficult to precisely arrange nerve cells on a substrate by a manual procedure.

SUMMARY OF THE INVENTION

In Patent Document 1 (Japanese Unexamined Patent Application, First Publication No. 2019-162097), an attempt was made to arrange cells by using a pattern of a cell adhesive material and a cell non-adhesive material. However, the inventors of the present invention found that in a case where cells are arranged by using the pattern of a cell adhesive material and a cell non-adhesive material, it is difficult to cause cells to remain in a predetermined position since nerve cells in particular migrate in the cell adhesive portion. Therefore, an object of the present invention is to provide a technique for precisely arranging nerve cells on a substrate while suppressing the migration of nerve cells.

A manufacturing method for a substrate on which nerve cells are arranged, according to the present invention, includes a step of arranging, on a substrate, a plurality of liquid droplets containing nerve cells by an inkjet method to form one or a plurality of liquid pools, where the substrate has a region in which a cell adhesive material is arranged and a region in which a cell non-adhesive material is arranged; and a step of incubating the liquid pool until the nerve cells sediment and temporarily adhere onto the substrate to form a cell aggregate, where the diameter per one liquid pool is 500 µm or less and the density of nerve cells per one liquid pool is $10^5$ cells/cm$^2$ or more.

According to the present invention, a technique for precisely arranging nerve cells on a substrate while suppressing the migration of nerve cells can be provided.

BRIEF DESCRIPTION OF THE DRAWINGS

FIGS. 15A to 15E are schematic views illustrating a procedure of Experimental Example 5.

DETAILED DESCRIPTION OF THE INVENTION

Figure 1:
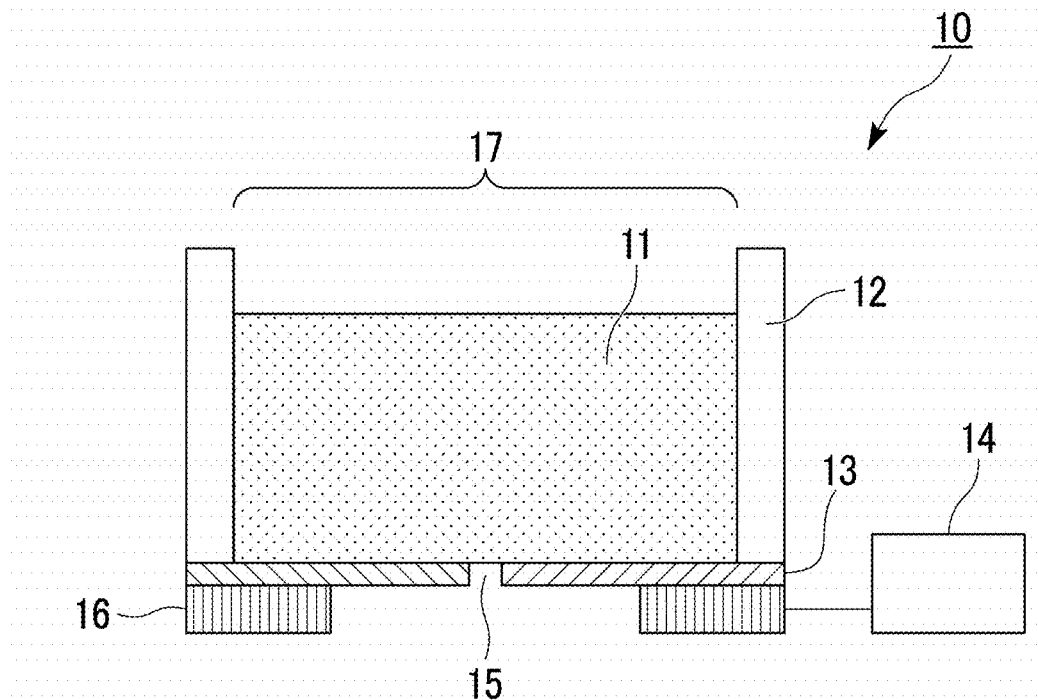
FIG. 1 is a schematic view illustrating one example of an inkjet head.

Hereinafter, embodiments of the present invention will be described in detail with reference to the drawings as necessary. In the drawings, the same or corresponding parts are designated by the same or corresponding reference numerals, and the description thereof will not be duplicated. The dimensional ratio in each figure may be exaggerated for illustration and thus may not necessarily match the actual dimensional ratio.

[Manufacturing Method for Substrate on which Nerve Cells are Arranged]

One embodiment of the present invention provides a manufacturing method for a substrate on which nerve cells are arranged, including a step of forming one or a plurality of liquid pools by arranging a plurality of liquid droplets containing nerve cells on a substrate using an inkjet method, to form one or a plurality of liquid pools, where the substrate has a region in which a cell adhesive material is arranged and a region in which a cell non-adhesive material is arranged; and a step of incubating the liquid pool until the nerve cells sediment and temporarily adhere onto the substrate to form a cell aggregate, where the diameter per one liquid pool is 500 µm or less and the density of nerve cells per one liquid pool is $10^5$ cells/cm$^2$ or more.

As will described below in Examples, the inventors revealed that in a case where the diameter per one liquid pool which is arranged on the substrate is 500 µm or less and the density of nerve cells in the liquid pool is $10^5$ cells/cm$^2$ or more, the migration of nerve cells is suppressed and the nerve cells can be precisely arranged on the substrate. Further, in a case where a liquid droplet containing cells is ejected onto a substrate by an inkjet method, the cells can be stably arranged in the unit of several cells in a fine region in the order of magnitude of micrometers.

The diameter per one liquid pool may be 400 µm or less, 300 µm or less, or 200 µm or less. It is preferable to reduce the diameter of the liquid pool since it is easy to reduce the number of expensive cells to be used.

Here, the liquid droplet means a liquid droplet ejected from an inkjet head by the inkjet method. In addition, the liquid pool means a liquid droplet formed by landing a plurality of liquid droplets ejected from the inkjet head on the substrate. Further, the diameter per one liquid pool refers to the diameter of a region in which one liquid pool is in contact with the substrate. In a case where the region in which the liquid pool is in contact with the substrate is not circular, a circle having the same area as the region in which the liquid pools are in contact with the substrate is assumed, and the diameter thereof is used. The density of nerve cells per one liquid pool refers to the number of cells per area in which one liquid pool is in contact with the substrate.

The above liquid droplets preferably contain 1 to 50 nerve cells per one liquid droplet. In addition, the number of nerve cells contained in one liquid pool is preferably about 7 to 10,000. The number of nerve cells contained in one liquid pool may be 7 or more, 30 or more, or 70 or more. In addition, the number of nerve cells contained in one liquid pool may be 100 or less, 70 or less, or 30 or less. The upper limit and the lower limit thereof can be combined randomly.

The substrate is not particularly limited as long as it can be used for cell culture, and examples of the substrate material include organic materials and inorganic materials described below. These may be used alone or in a combination of two or more thereof.

The organic material is not particularly limited and may be appropriately selected depending on the intended purpose. Examples thereof include polyethylene terephthalate (PET), polystyrene (PS), polycarbonate (PC), triacetyl cellulose (TAC), polyimide (PI), nylon (Ny), low-density polyethylene (LDPE), medium-density polyethylene (MDPE), vinyl chloride, vinylidene chloride, polyphenylene sulfide, polyether sulfone, polyethylene naphthalate, polypropylene, an acrylic material such as urethane acrylate, cellulose, a silicone-based material such as polydimethylsiloxane (PDMS), polyvinyl alcohol (PVA), a metal alginate salt such as calcium alginate, and gel-like materials such as polyacrylamide, methyl cellulose, and agarose.

The inorganic material is not particularly limited and may be appropriately selected depending on the intended purpose. Examples thereof include glass and ceramics.

The structure of the substrate is not particularly limited as long as it can be used for cell culture, and examples thereof include a porous structure and a non-porous structure. The substrate may be a substrate having a porous structure or may be a substrate having a non-porous flat plate member in which a porous member is laminated.

The size and the shape of the fine pores of the porous structure are not limited and, for example, a mesh structure, an uneven structure, a honeycomb structure, or the like may be adopted. The substrate structure is preferably a porous structure since the surface area on which a cell non-adhesive material or a cell adhesive material is fixed is large, a large amount of solution can be retained, and drying can be suppressed.

In a case where a substrate having a porous structure is used as the substrate and a liquid pool is formed in a state where a liquid such as a medium is retained in the substrate in advance, the liquid is retained by the above-described porous structure, and thus drying of the liquid pool can be suppressed.

Further, in a case where liquid droplets are ejected onto the dried substrate to form a liquid pool, the shape of the liquid pool can be maintained and the adhesion of the cells on the substrate can be stably achieved by carrying out a step of suppressing the evaporation of the liquid in the liquid pool (drying-suppressing step).

Examples of the drying-suppressing step include (i) a step of increasing the humidity in the vicinity of the liquid pool, (ii) a step of forming the liquid pool after arranging a fluid that suppresses evaporation of the liquid on the substrate (here, examples of the fluid that suppresses evaporation of the liquid include oil, medium, and a buffer solution), (iii) a step of coating the liquid pool with a fluid (for example, oil) that suppresses evaporation of the liquid after forming the liquid pool on the substrate.

In a case where the suppression of evaporation is carried out by increasing the humidity, it is preferable to perform local humidity control in order to minimize the influence on the surroundings. In addition, in a case where oil is used to suppress drying, it is preferable to use oil that has biocompatibility in terms of suppressing the influence on cells.

The manufacturing method of the present embodiment may further include a step of supplying a medium to the substrate on which the cell aggregate is formed. As the medium, a medium suitable for the cells to be used can be appropriately selected and used. Specific examples of the medium include Dulbecco's modified Eagle's medium (DMEM), Ham's F-12 medium (Ham's Nutrient Mixture F12), D-MEM/F12 medium, McCoy's 5A medium, Eagle's minimum essential medium (EMEM), alpha modified Eagle's minimum essential medium (aMEM), Minimum essential medium (MEM), Roswell Park Memorial Institute-1640 medium (RPMI 1640), Iscove's modified Dulbecco's medium (IMDM), MCDB 131 medium, William's medium E, IPL41 medium, Fischer's medium, M199 medium, High Performance Medium 199, StemPro-34 (manufactured by Thermo Fisher Scientific, Inc.), X-VIVO 10 (manufactured by Chembrex), X-VIVO 15 (manufactured by Chembrex), HPGM (manufactured by Chembrex), StemSpan H3000 (manufactured by STEMCELL Technologies), StemSpan SFEM (manufactured by STEMCELL Technologies), Stemline II (manufactured by Sigma-Aldrich Co., LLC), QBSF-60 (manufactured by Quality Biological, Inc.), StemPro hESCSFM (manufactured by Thermo Fisher Scientific, Inc.), Essential 8 (registered trade mark) medium (manufactured by Thermo Fisher Scientific, Inc.), mTeSR1 or mTeSR2 medium (manufactured by STEMCELL Technologies), ReproFF or ReproFF2 (manufactured by ReproCELL Inc.), PSGro hESC/iPSC medium (manufactured by System Biosciences, LLC), NutriStem (registered trade mark) medium (manufactured by Biological Industries), CSTI-7 medium (manufactured by Cell Science & Technology Institute, Inc.), MesenPRO RS medium (manufactured by Thermo Fisher Scientific, Inc.), MF-medium (registered trade mark) mesenchymal stem cell growth medium (manufactured by TOYOBO Co., Ltd.), Sf-90011 (manufactured by Thermo Fisher Scientific, Inc.), and Opti-Pro (manufactured by Thermo Fisher Scientific, Inc.).

These may be used alone, or two or more thereof may be mixed and used. In particular, in the case of DMEM/F12 medium, it is preferable to mix DMEM medium with F12 medium in the range of 6:4 to 4:6 in terms of the mass ratio.

In addition, an additive may be added to the medium. Examples of the additives include those generally used for nerve cell culture, examples of which include SM1 supplement (STEMCELL Technologies), N2 supplement A (STEMCELL Technologies), rat astrocyte culture supernatant (FUJIFILM Wako Pure Chemical Corporation), human astrocyte culture supernatant (ScienCell Research Laboratories, Inc.), Component N (Elixirgen Scientific, Inc.), Component G2 (Elixirgen Scientific, Inc.), Component P (Elixirgen Scientific, Inc.), N2 Supplement B (Thermo Fisher Scientific, Inc.), iCell Neural Supplement B (manufactured by FujiFilm Cellular Dynamics, Inc.), and B-27 Plus Neuronal Culture System (Thermo Fisher Scientific, Inc.).

In addition, the manufacturing method of the present embodiment may further include a step of functionally binding at least two cell aggregates by incubating the substrate to which the medium has been supplied, in which a plurality of the liquid pools are formed in the step of forming the liquid pool and a plurality of the cell aggregates are formed in the step of incubating.

In a case where a plurality of liquid pools are formed on the substrate, a cell aggregate is formed in each liquid pool. Then, as a result of supplying a medium to these cell aggregates and performing incubation, at least two of the cell aggregates are functionally bound and a neural circuit model can be produced. Here, the functional connection between the cell aggregates means that a nerve cell extends a protrusion called an axon, which forms a synaptic connection with a dendrite of another nerve cell. As a result, a neural circuit is formed.

Nerve cells can also be roughly divided into, for example, a peripheral nerve and a central nerve. Examples of the peripheral nerve include a sensory nerve cell, a motor nerve cell, and an autonomous nerve cell. Examples of the central nerve include an interneuron and a projection neuron. Examples of the projection neuron include a cortical neuron, a hippocampal neuron, an amygdala neuron. In addition, the central nerve cells can be roughly divided into an excitatory neuron and an inhibitory neuron. Examples thereof include a glutamatergic neuron mainly responsible for excitatory transmission in the central nerve system and a γ-aminobutyric acid-dependent (GABAergic) neuron mainly responsible for inhibitory transmission.

Examples of other neurons that release a neuromodulator include a cholinergic neuron, a dopaminergic neuron, a noradrenergic neuron, a serotonergic neuron, and a histaminergic neuron.

In the manufacturing method of the present embodiment, a cell aggregate containing cells other than nerve cells may be further arranged on the substrate on which the nerve cells are arranged. A cell aggregate other than the cell aggregate containing nerve cells may include a cell capable of receiving a transmission signal from a nerve cell. Examples of the cell that can receive a transmission signal from a nerve cell include a nerve cell and a muscle cell. Examples of muscle cells include a myocardial cell, a skeletal muscle cell, and a smooth muscle cell. These cells may be used alone or in a combination of two or more kinds thereof.

In the manufacturing method of the present embodiment, the nerve cell may be a primary cultured cell, may be a subcultured cell, may be an established cell line, may be an immortalized cell, or may be a nerve cell that has undergone gene editing with various genes. Further, from the viewpoint of easily obtaining a cell population containing a large amount of desired nerve cells, the nerve cell may be a nerve cell differentiated from a stem cell.

Examples of stem cells include an embryonic stem cell (an ES cell), an induced pluripotent stem cell, a mesenchymal stem cell, a cord blood-derived stem cell, and a nerve stem cell. Examples of the induced pluripotent stem cell include a nuclear-transplanted embryonic stem cell (a ntES cell) and an induced pluripotent stem cell (an iPS cell). Examples of mesenchymal stem cells include a bone marrow mesenchymal stem cell and an adipose tissue-derived mesenchymal stem cell. Among them, an iPS cell is preferable as a stem cell.

The iPS cell may be derived from a healthy person or patients having various diseases of the nerve system. Further, the iPS cell may be a cell that has undergone gene editing with various genes and may be, for example, a cell that has undergone gene editing and has a gene that is a cause or risk factor of various diseases of the nerve system.

In a case where the iPS cell is a cell derived from patients having various diseases of the nerve system, the iPS cells can be used to construct a disease model of the nervous system of the patients. The disease of the nerve system is not particularly limited, but examples thereof include neurodegenerative disease, autism, epilepsy, attention-deficit hyperactivity disorder (ADHD), schizophrenia, and bipolar disorder. Examples of the neurodegenerative disease include Alzheimer's disease, Parkinson's disease, and amyotrophic lateral sclerosis.

The animal species from which nerve cells are derived is not particularly limited, and examples thereof include humans, monkeys, dogs, cows, horses, sheep, pigs, rabbits, mice, rats, guinea pigs, and hamsters. Of them, humans are preferable.

In the manufacturing method of the present embodiment, the nerve cells may be those collected from a living body, those that have been established and cultured, or those that have been induced to differentiate from a stem cell.

In a case where a neural circuit model is produced using a plurality of kinds of nerve cells, it is preferable that one cell aggregate contain one kind of nerve cell. In addition, each of the plurality of cell aggregates may contain different kinds of nerve cells depending on the intended purpose.

Hereinafter, a step of arranging liquid droplets containing nerve cells on a substrate to form one or a plurality of liquid pools will be described. This step is performed by ejecting a cell suspension (a cell ink) containing at least nerve cells and a cell-drying inhibitor, as the liquid droplet, by an inkjet system.

Examples of the liquid droplet ejection means by the inkjet system include a so-called piezo method (for example, see Japanese Examined Patent Application, Second Publication No. H02-51734) in which a piezoelectric element is used, as a pressure-generating means for pressurizing a cell ink, to change a volume of a cell suspension, thereby ejecting a liquid droplet; a so-called thermal method (for example, see Japanese Examined Patent Application, Second Publication No. S61-59911) in which a cell ink is heated using a heat-generating resistor to generate bubbles; and an electrostatic method (for example, see Japanese Unexamined Patent Application, First Publication No. H06-71882) in which a diaphragm and an electrode are arranged to face each other and the diaphragm is deformed by the electrostatic force generated between the diaphragm and the electrode, whereby a volume of a cell ink is changed and liquid droplets are ejected.

(Inkjet Head)

Figure 2:
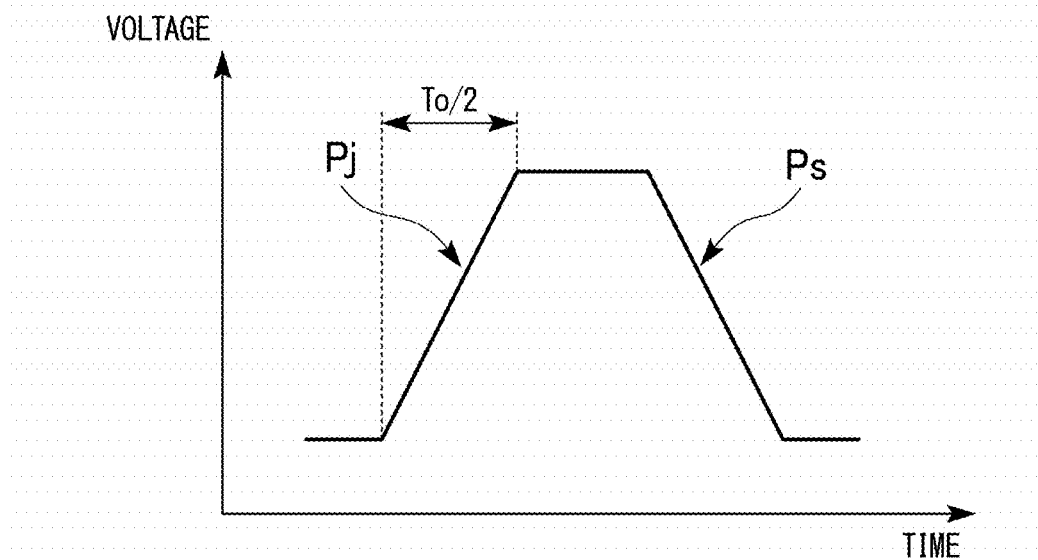
FIG. 2 is a schematic view illustrating one example of an input waveform to an inkjet head.
Figure 3:
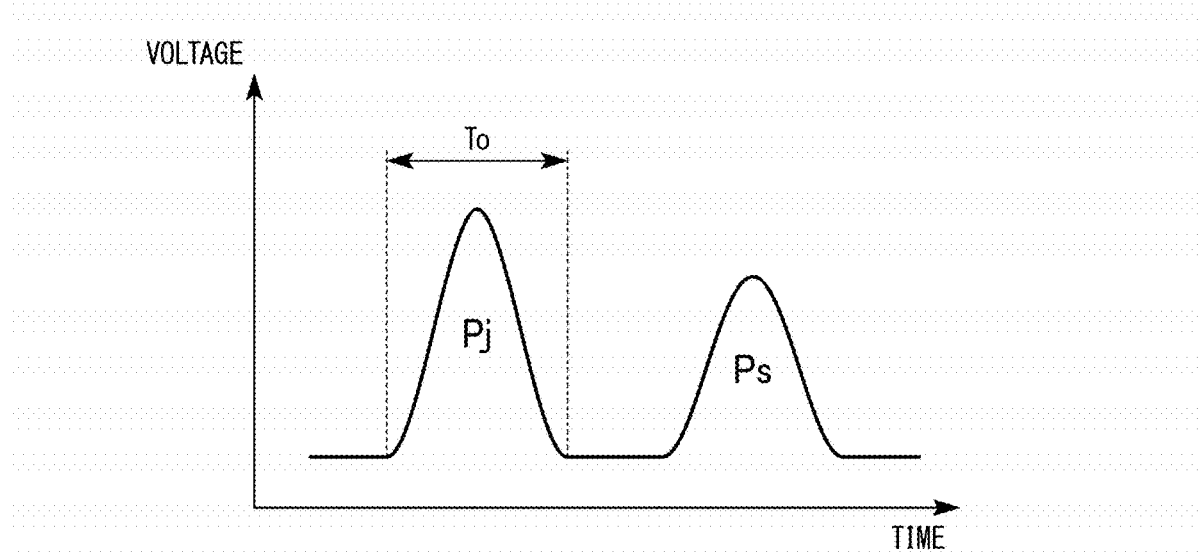
FIG. 3 is a schematic view illustrating one example of an input waveform to an inkjet head.

A specific aspect of an inkjet head that is used for ejecting a cell ink containing nerve cells and a cell-drying inhibitor, as the liquid droplet, will be described below. FIG. 1 is a schematic view illustrating one example of an inkjet head. In FIG. 1, a piezoelectric element is used as the pressure-generating means. FIG. 2 and FIG. 3 are schematic views illustrating one example of an input waveform to an inkjet head.

A liquid droplet ejection head 10 has a liquid chamber 12 that retains a cell ink 11, a nozzle 15, a membrane 13 that is a film-shaped member, a vibration application portion 16 that applies vibration to the membrane 13, and a driving unit 14 that applies a voltage to the vibration application portion 16 as a specific driving signal in order to vibrate the vibration application portion 16.

In the liquid chamber 12, an atmospheric opening portion 17 for opening the liquid chamber to the atmosphere is provided. In the liquid droplet ejection head 10, in a case where vibration is applied to the cell ink, liquid droplets of the cell ink are ejected from the nozzle.

The driving unit 14 can add an ejection waveform Pj to the vibration application portion 16 as a driving signal to control the vibration state of the membrane 13, whereby the cell ink 11 retained in the liquid chamber 12 can be ejected in a liquid droplet shape. The ejection waveform Pj may be set to a driving signal including the natural vibration period To of the membrane 13 in order to resonate the membrane 13 and eject the cell ink 11 at a lower voltage. As the ejection waveform Pj, not only a triangular wave and a sine wave but also a triangular wave whose edge is rounded by applying a low-pass filter can be used. Further, the driving unit 14 can add a vibration isolation waveform Ps that suppresses the residual vibration of the membrane after liquid droplets are ejected, to the vibration application portion 16 as a driving signal. As a result, the residual vibration of the membrane after the formation of liquid droplets is suppressed rapidly, and thus continuous ejection at a higher frequency is possible. Further, in a case where satellites and mist are reduced, control of liquid droplets of a smaller amount is possible. As the vibration isolation waveform Ps, not only a triangular wave and a sine wave but also a triangular wave whose edge is rounded by applying a low-pass filter can be used.

The amount of the cell ink 11 retained in the liquid chamber 12 is not particularly limited, and for example, it is possible to retain a liquid of about 1 µL to 1 mL. In particular, in a case where an expensive liquid such as a cell ink in which cells are dispersed is used, it is preferable that liquid droplets be formed with a small amount of liquid, and that a configuration in which a liquid amount of about 1 µL to 50 µL can be retained may be used.

The shape of the membrane 13 may be circular, elliptical, or quadrangular. The material of the membrane 13 is not particularly limited. However, in a case of being too soft, the membrane easily vibrates, and it is difficult to immediately suppress the vibration when liquid droplets are not ejected. For this reason, it is advantageous for the material to have a certain degree of hardness. As the material of the membrane 13, for example, a metal material, a ceramic material, or a polymer material having a certain degree of hardness can be used.

It is preferable that the nozzle 15 be formed as a substantially circular through-hole in the center of the membrane 13. Examples of the vibration application portion 16 include a piezoelectric element. In a case where a voltage is applied, compressive stress is applied in the lateral direction of the paper surface, and thus the membrane 13 can be deformed. As the material of the piezoelectric element, for example, a commonly used lead zirconate titanate can be used. In addition to this, various piezoelectric materials such as a bismuth iron oxide, a metal niobate, and barium titanate, or materials obtained by adding a metal or a different oxide to these materials can be used.

The means for applying vibration to the membrane 13 for deforming the membrane 13 is not limited to the piezoelectric element. For example, it is possible to use a material having a linear expansion coefficient different from that of the membrane, which is attached to the membrane 13 and is heated to deform the membrane 13 by utilizing the difference in linear expansion coefficient. In this case, for example, a heater is formed in the material having a different linear expansion coefficient, and the heater is heated by electricity so that the membrane 13 can be deformed.

(Cell Ink)

Next, the cell ink will be described. The cell ink contains at least nerve cells and a cell-drying inhibitor. Further, the cell suspension (the cell ink) contains a dispersion medium for dispersing cells and may contain other additive materials such as a dispersant and a pH-adjusting agent, as necessary. The nerve cells are the same as those described above.

The cell-drying inhibitor has a function of covering the surface of cells and suppressing drying of cells, and examples thereof include polyhydric alcohols, gel-like polysaccharides, and a protein selected from extracellular matrices.

The polyhydric alcohol is not particularly limited as long as it does not damage cells. Examples thereof include glycerin, diglycerin, diethylene glycol, 1,3-butanediol, 1,2,3-butanetriol, 1,2,4-butanetriol, triethylene glycol, tetraethylene glycol, propylene glycol, and polyethylene glycol. These may be used alone, or two or more thereof may be mixed and used. Among these, glycerin is preferable. Glycerin has low toxicity to cells and can be expected to have an effect of suppressing drying even at a low addition amount.

The gel-like polysaccharide means a polysaccharide having a gel state. The gel-like polysaccharide is not particularly limited and it may be appropriately selected depending on the intended purpose. Examples thereof include calcium alginate, gellan gum, agarose, guar gum, xanthan gum, carrageenan, pectin, locust bean gum, tamarind gum, diutan gum, and carboxymethyl cellulose. These may be used alone, or two or more thereof may be mixed and used. Among these, calcium alginate is preferable. Calcium alginate is a salt, in which a calcium ion is bonded to a carboxyl group in alginic acid, and thickens since calcium is bonded (ion-crosslinked) across two carboxyl groups due to the fact that a calcium ion is divalent, whereby the drying of the cell ink can be suppressed. In this case, calcium ions are contained in the dispersion medium, and calcium ions that have become excessive due to concentration by drying are considered to be bonded and are expected to play a role in adjusting the osmotic pressure.

The protein selected from the extracellular matrices is not particularly limited and it may be appropriately selected depending on the intended purpose. Examples thereof include collagen, laminin, fibronectin, elastin, and fibrin. These may be used alone, or two or more thereof may be mixed and used. Among these, collagen is preferable. Various types of collagen are known and the viscosity thereof increases depending on the concentration and temperature. In a case where collagen is incorporated in a cell ink, it is possible to cause collagen to thicken in a case where the concentration of collagen increases.

As the dispersion medium, a medium for cell culture or a buffer solution is preferable. The medium is the same as that described above. The buffer solution is used for adjusting pH, and a conventionally known buffer solution can be appropriately selected and used.

Since the amount of the liquid pool arranged on the substrate is very small, the liquid in the liquid pool evaporates in several tens of seconds to several minutes, and the concentration of the components in the liquid pool rises drastically. The drastic change in osmotic pressure or the like caused by this concentration change damages cells in the liquid pool, and in the worst case, cell death occurs. Accordingly, it is preferable to suppress the evaporation of the liquid in the liquid pool by the following method.

For example, in a case where a substrate having a porous structure is used as the substrate and a liquid pool is formed in a state where a liquid such as a medium is retained in the substrate in advance, the liquid is retained by the above-described porous structure, and thus drying of the liquid pool can be suppressed.

Further, in a case where liquid droplets are ejected onto the dried substrate to form a liquid pool, the shape of the liquid pool can be maintained and the adhesion of the cells on the substrate can be stably achieved by carrying out a step of suppressing the evaporation of the liquid in the liquid pool (drying-suppressing step). Examples of the drying-suppressing step include the same steps as those described above.

(Step of Arranging Liquid Droplets)

Next, a step of arranging one or more liquid droplets containing cells on a substrate to form one or more liquid pools will be described. In the step of arranging liquid droplets, liquid droplets of a cell ink are ejected to a target position on the substrate. The liquid droplets containing nerve cells may be arranged at one place on the substrate or may be arranged at a plurality of positions on the substrate. A plurality of liquid droplets of cell ink ejected from the inkjet head are arranged at one place on the substrate to form one liquid pool.

In a case where the timing of ejecting the liquid droplets is adjusted, the position of the cells that have adhered to the region (cell adhesive portion) in which the cell adhesive material is arranged can be adjusted. In addition, in a case where the ejection amount (the number of liquid droplets or the liquid droplet amount) or the cell concentration of the cell ink is adjusted at this time, the number of cells arranged on the substrate can be adjusted.

The cells in the liquid pool, which are arranged on the substrate, sediment and temporarily adhere onto the substrate to form a cell aggregate. According to the inkjet method, since the liquid droplet of the cell ink is very small compared to the manual procedure, the time until the cells temporarily adhere onto the substrate is very short. Further, in a case where the liquid droplet is arranged by the inkjet method, the shape accuracy of the cell pattern in which nerve cells are arranged at predetermined positions is high. The probability that a predetermined number of nerve cells can be arranged at a predetermined position or the probability that the number of arranged cells is the desired number is high, and the accuracy of arranging the desired number of nerve cells is high. In addition, the survival rate of the arranged nerve cells after a lapse of a predetermined time is also high.

(Liquid Droplet-Arranging Device)

Hereinafter, specific aspects of a device for arranging liquid droplets on a substrate (hereinafter, may be referred to as a "liquid droplet-arranging device") will be described. However, the present invention is not limited to these aspects.

The liquid droplet-arranging device includes a stage portion and an inkjet head which is the liquid droplet ejection means for ejecting liquid droplets of the cell ink. The stage portion retains the substrate. The configuration of the liquid droplet ejection head is the same as that of the inkjet head described above.

One example of the liquid droplet-arranging device equipped with an inkjet head is illustrated in FIG. 4 to FIG. 7. The liquid droplet-arranging device 400 illustrated in FIG. 4 has a stage portion 31 and an inkjet head 21. As described above, the inkjet head 21 has a liquid chamber 25, a vibration application portion 27, a driving unit 26, and a membrane 28. Further, in the inkjet head 21, an atmospheric opening portion 24 is formed.

Figure 5:
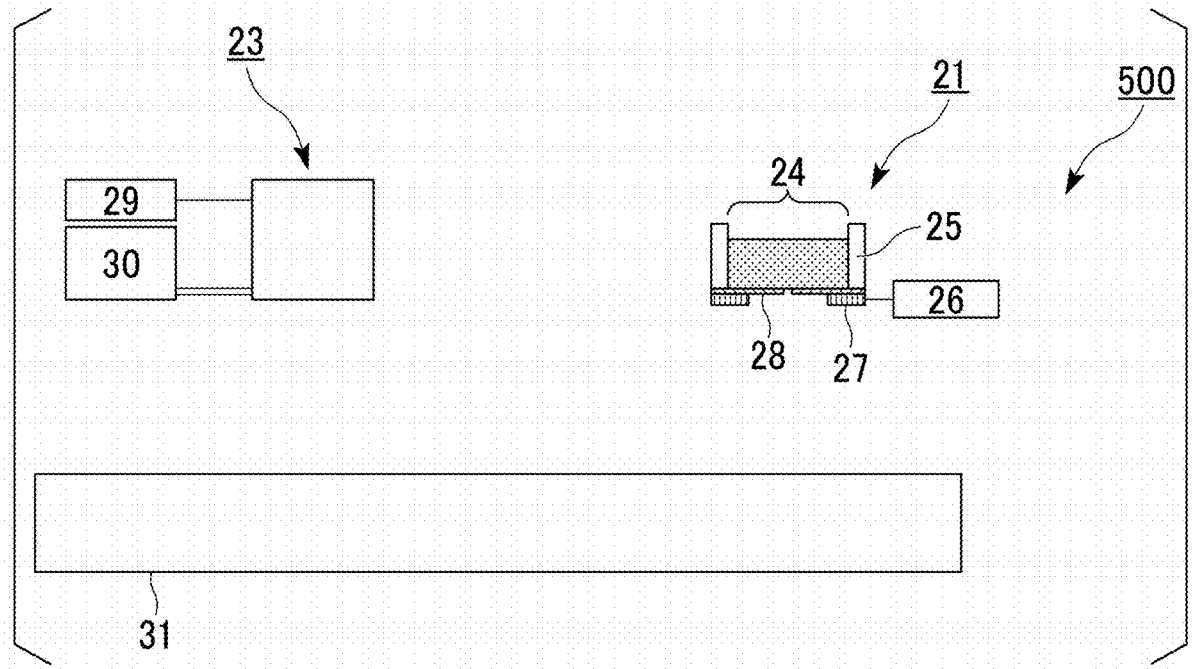
FIG. 5 is a schematic view illustrating one example of a liquid droplet-arranging device.

The liquid droplet-arranging device may be configured to be capable of ejecting not only a cell ink but also liquid droplets of a solution containing a cell non-adhesive material or a cell adhesive material. The liquid droplet-arranging device 500 illustrated in FIG. 5 includes an inkjet head 23 that ejects liquid droplets of the solution containing a cell non-adhesive material or a cell adhesive material, in addition to the inkjet head 21 that ejects liquid droplets of the cell ink. The basic configuration of the inkjet head 23 is the same as that of the inkjet head 21. In FIG. 5, a reference numeral 29 indicates a driving unit, and a reference numeral 30 indicates a liquid chamber for retaining a solution of a cell non-adhesive material or a cell adhesive material. Like the inkjet head 21, the inkjet head 23 has a vibration application portion and a membrane (not illustrated in the figure).

Figure 6:
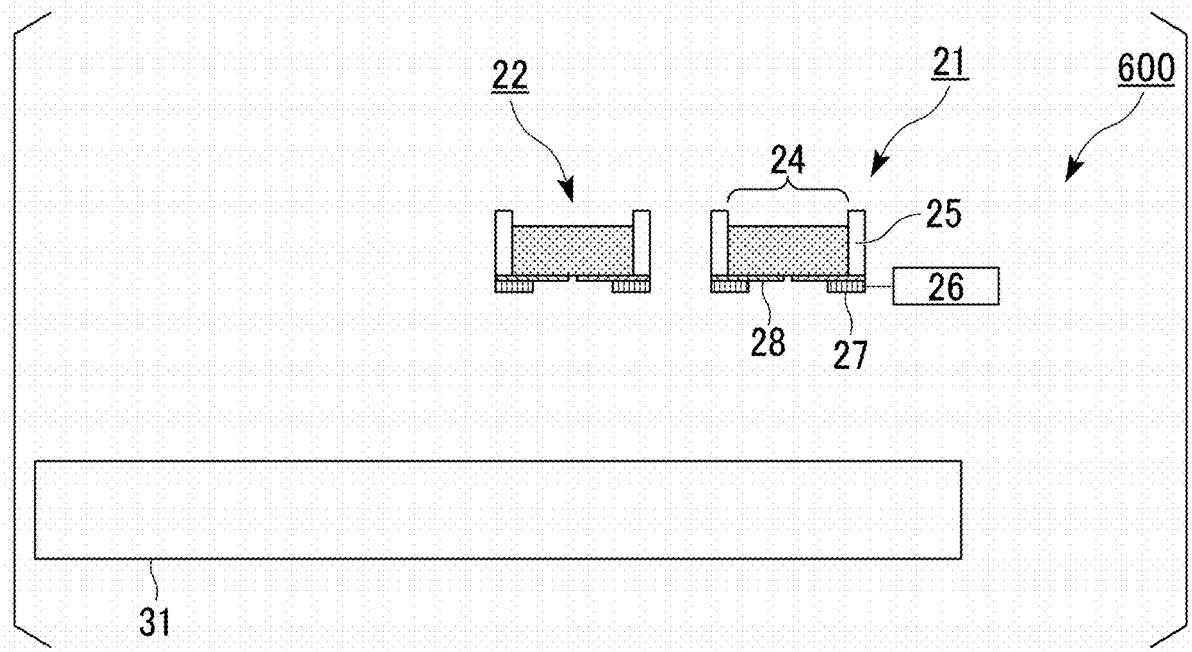
FIG. 6 is a schematic view illustrating one example of a liquid droplet-arranging device.
Figure 7:
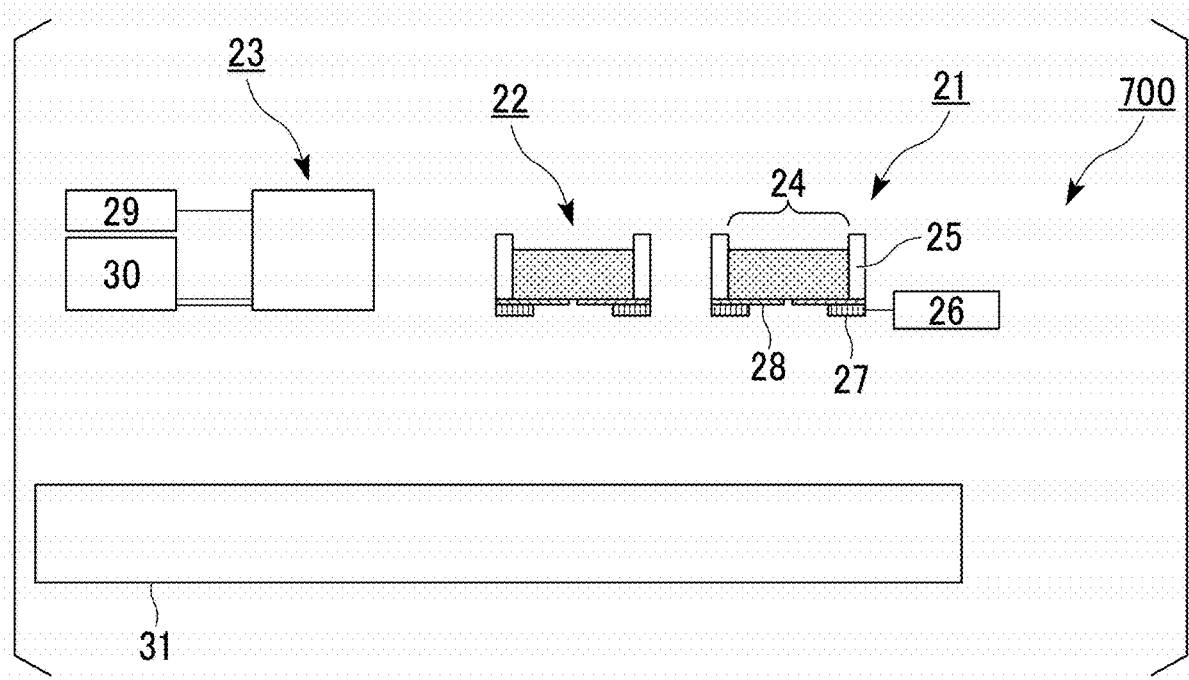
FIG. 7 is a schematic view illustrating one example of a liquid droplet-arranging device.

The liquid droplet-arranging device can also arrange liquid droplets containing two or more kinds of cells. The liquid droplet-arranging device 600 illustrated in FIG. 6 can include a plurality of inkjet heads 21 that eject liquid droplets of the cell ink. In FIG. 6, an example in which the inkjet head 21 and an inkjet head 22 having the same configuration as the inkjet head 21 are provided is illustrated. Further, in FIG. 7, a liquid droplet-arranging device 700 including an inkjet head 23 in addition to the inkjet heads 21 and 22 is illustrated. In addition to the above-described configuration, the liquid droplet-arranging device may include a retaining portion for retaining the inkjet head, a mechanical portion for controlling the relative position between the stage and the inkjet head, and the like.

The substrate on which nerve cells are arranged has a region in which the cell adhesive material is arranged and a region in which a cell non-adhesive material is arranged. In the present specification, the region in which the cell adhesive material is arranged may be referred to as a cell adhesive portion. Further, a region in which the cell non-adhesive material is arranged may be referred to as a cell non-adhesive portion. As described later in Examples, in a case where a pattern of the cell non-adhesive material is arranged on the surface of the substrate, it is possible to more flexibly control axon extension in a case where nerve cells are arranged.

In a case where the cell non-adhesive material is arranged on the substrate, the growth direction of the cells can be defined. Further, in a case where the cell non-adhesive material is arranged on the substrate, a plurality of kinds of cells are arranged without being mixed with each other. Here, in a case where the plurality of kinds of cells are arranged by the inkjet method, it is preferable to independently prepare one inkjet head that ejects liquid droplets of the cell ink for one kind of cell, from the viewpoint of avoiding contamination between cells.

The pattern of the cell non-adhesive material has a region in which the cell non-adhesive material is arranged and a region in which the cell non-adhesive material is not arranged, where the region in which the cell non-adhesive material is not arranged may have a linear shape. In this case, the width of the linear shape is preferably 100 µm or less.

In a case where the width of the linear shape is 100 µm or less, the axon can be extended along the linear shape in which the cell non-adhesive material is not arranged. That is, the region sandwiched between two patterns of the cell non-adhesive material, which have a linear shape, can be used as a pathway for axons to be extended.

A pattern of the cell non-adhesive material is arranged and further a pattern of the cell adhesive material is arranged on the surface of the substrate on which cells are arranged. Liquid droplets of cell ink may be arranged to be in contact with the cell adhesive material. In a case where the liquid droplets of the cell ink are arranged to be in contact with the cell adhesive material and the area of the pattern of the cell adhesive material is smaller than the area in which the liquid pool of the cell ink is arranged on the substrate and is in contact with the substrate, the cells contained in the liquid droplets sediment and temporarily adhere onto the substrate, and then tend to move and aggregate on the pattern of the cell adhesive material. Accordingly, the arrangement of cells can be controlled by arranging the pattern of the cell adhesive material on the substrate.

(Cell Non-Adhesive Material)

Examples of the cell non-adhesive material include polydimethylsiloxane (PDMS), a gel of an alginate metal salt (calcium alginate or the like), polyhydroxyethyl methacrylate (pHEMA), polyethylene glycol (PEG), and derivatives thereof.

Here, a case where the cell non-adhesive material is polyethylene glycol will be described. In this case, for example, a first solution which contains a multi-branched polymer having polyethylene glycol as a skeleton and one of at least one nucleophilic functional group and at least one electrophilic functional group at the side chains and/or terminals is brought into contact with a second solution which contains a multi-branched polymer having polyethylene glycol as the skeleton and the other of at least one nucleophilic functional group and at least one electrophilic functional group at the side chains and/or terminals, whereby these solutions can be crosslinked to form a pattern of the cell non-adhesive material.

The "multi-branched polymer having polyethylene glycol as the skeleton" (hereinafter, may be simply referred to as the "multi-branched polymer" or the "Multi-Arm PEG") is a polymer used as a gelling material. In a case where two kinds of Multi-Arm PEGs respectively having a nucleophilic functional group and an electrophilic functional group are crosslinked with each other at the terminals of a plurality of polyethylene glycol (PEG) branches, a gel (a Multi-Arm PEG gel) having a network structure can be formed.

For example, in a case of two kinds of tetra-branched polymers (hereinafter, may be referred to as a "Tetra-PEG") respectively having a nucleophilic functional group and an electrophilic functional group at the terminals of the four PEG branches, a gel called "Tetra-PEG gel" having a uniform network structure can be formed.

The number of branches of the multi-branched polymer is not particularly limited. Generally, there is no problem as long as PEGs have three or more branches respectively containing an electrophilic terminal and a nucleophilic terminal and can be appropriately selected as necessary. The two or more PEGs constituting the Multi-Arm PEG may have different numbers of branches as long as they respectively have a nucleophilic functional group and an electrophilic functional group. Among the Multi-Arm PEGs, a Tetra-PEG gel is known to have an ideal uniform network structure.

Further, the Tetra-PEG gel can be easily and quickly formed on the spot by simply mixing two kinds of Tetra-PEGs respectively contained in the first solution and the second solution, and further, the pH and the concentration of each Tetra-PEG can be adjusted, whereby the gelation time can also be controlled. In addition, biocompatibility is excellent since the main component is PEG. In a case where two kinds of Tetra-PEGs are reacted to form a Tetra-PEG gel by ejecting solutions containing cells and respective Tetra-PEGs with a liquid droplet ejection device, it is possible to arrange cells in three dimensions.

As one embodiment, a Tetra-PEG may be a compound having a structure represented by Formula (1).

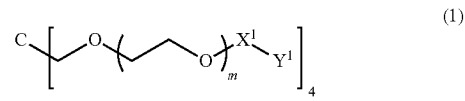

(1)

In Formula (1), m's may be the same or different from each other. The closer the values of m's are, the more uniform a three-dimensional structure obtained, and the higher the strength of the gel. Therefore, in order to obtain a gel having high strength, it is preferable that m's be the same. In a case where the value of each m is too high, the strength of the gel will be weakened, and in a case where the value of each m is too low, it is difficult to form a gel due to the steric hindrance of the compound. Therefore, as the value of each m, an integer value of 25 to 250 is preferable, and a value of each m is more preferably 35 to 180, further preferably 50 to 115, and particularly preferably 50 to 60. Examples of the molecular weight thereof include $5 \times 10^3$ to $5 \times 10^4$ Da, and $7.5 \times 10^3$ to $3 \times 10^4$ Da is preferable, and $1 \times 10^4$ to $2 \times 10^4$ Da is more preferable.

In Formula (1), $X^1$ is a linker moiety connecting a functional group and a core part. $X^1$'s may be the same or different from each other but are preferably the same in order to produce a gel having high strength and a uniform three-dimensional structure. $X^1$ represents a $C_1$-$C_7$ alkylene group, a $C_2$-$C_7$ alkenylene group, —NH—Ra—, —CO—Ra—, —Rb—O—Rc-, —Rb—NH—Re—, —Rb—$CO_2$—Rc-, —Rb—$CO_2$—NH—Rc-, —Rb—CO—Re—, or —Rb—CO—NH—Rc-. Here, Ra represents a $C_1$-$C_7$ alkylene group, Rb represents a $C_1$-$C_3$ alkylene group, and Rc represents a $C_1$-$C_5$ alkylene group.

The "$C_1$-$C_7$ alkylene group" is an alkylene group which has 1 or more and 7 or less carbon atoms and may have a branch including a linear $C_1$-$C_7$ alkylene group or a $C_2$-$C_7$ alkylene group (having 2 or more and 7 or less carbon atoms, including carbon atoms of the branch thereof) having one or more branches. Examples of the $C_1$-$C_7$ alkylene group include a methylene group, an ethylene group, a propylene group, and a butylene group. Examples of the $C_1$-$C_7$ alkylene group include —$CH_2$—, —$(CH_2)_2$—, —$(CH_2)_3$—, —CH(CH$_3$)—, —(CH(CH$_3$))$_2$—, —(CH$_2$)$_2$—CH(CH$_3$)—, —(CH$_2$)$_3$—CH(CH$_3$)—, —(CH$_2$)$_2$—CH(C$_2$H$_5$)—, —(CH$_2$)$_6$—, —(CH$_2$)$_2$—C(C$_2$H$_5$)$_2$—, and —(CH$_2$)$_3$C(CH$_3$)$_2$CH$_2$—.

The "C$_2$-C$_7$ alkenylene group" is a linear or branched alkenylene group having 2 to 7 carbon atoms and has one or more double bonds in the chain. Examples thereof include a divalent group having a double bond formed by removing 2 to 5 hydrogen atoms from adjacent carbon atoms of an alkylene group.

In Formula (1), as described above, $Y^1$ is a functional group for forming a network structure by a cross-end coupling reaction, which is a cross-linking reaction by a covalent bond and is selected from a nucleophilic functional group or an electrophilic functional group.

The "nucleophilic functional group" is not limited, but, for example, is preferably a thiol group from the viewpoint of shortening the gelation time. These functional groups may be the same or different from each other; however, they are preferably the same. In a case where the functional groups are the same, the reactivity with the nucleophilic functional group as the target of the cross-linking reaction becomes uniform, and it is easy to obtain a gel having high strength and a uniform three-dimensional structure. Hereinafter, a Tetra-PEG having a nucleophilic functional group may be referred to as a "nucleophilic Tetra-PEG".

The "electrophilic functional group" is not limited, but, for example, is preferably a maleimidyl group from the viewpoint of shortening the gelation time. These functional groups may be the same or different from each other; however, they are preferably the same. In a case where the functional groups are the same, the reactivity with the nucleophilic functional group as the target of the cross-linking reaction becomes uniform, and it is easy to obtain a gel having high strength and a uniform three-dimensional structure. Hereinafter, a Tetra-PEG having an electrophilic functional group may be referred to as an "electrophilic Tetra-PEG".

The nucleophilic Tetra-PEG and the electrophilic Tetra-PEG may be mixed so that the molar ratio of the nucleophilic functional group to the electrophilic functional group is 0.5:1 to 1.5:1. Since each of the functional groups can react 1:1 and crosslink, it is preferable that the mixing molar ratio be close to 1:1, but 0.8:1 to 1.2:1 is preferable for forming a hydrogel having high strength. Further, in a case where the pH of the dispersion medium in the first or the second solution is 5 to 10, the concentration of the Tetra-PEG contained in each solution may be in the range of 0.3% to 20%, and in a case where the pH is 6 to 10, the concentration thereof is preferably in the range of 1.7% to 20%.

The first solution may be composed of one of the nucleophilic Tetra-PEG and the electrophilic Tetra-PEG, and the second solution may be composed of the other of the nucleophilic Tetra-PEG and the electrophilic Tetra-PEG.

<<First Solution>>

The "first solution" is an aqueous solution containing a multi-branched polymer which has, as the skeleton, any one of a polyethylene glycol having at least one nucleophilic functional group or a polyethylene glycol having at least one electrophilic functional group at the side chain and/or at the terminal, and a dispersion medium as constitutional elements. The first solution can contain cells and a cell action additive, as necessary.

There may be a plurality of kinds of first solutions. In that case, the multi-branched polymer which has, as the skeleton, any one of polyethylene glycol having at least one nucleophilic functional group or polyethylene glycol having at least one electrophilic functional group, at the side chain and/or at the terminal, the dispersion medium, the cells, and the cell action additive, which are contained in each of the first solutions, may differ overall or in part. For example, a dispersion medium contained in a first solution a and a dispersion medium contained in a first solution b may be the same or different from each other. In a case where a plurality of kinds of first solutions are present, for example, the dispersion medium can be randomly changed in each layer when the hydrogels are laminated.

<<Second Solution>>

The "second solution" is an aqueous solution containing a multi-branched polymer which has a polyethylene glycol as the skeleton and one or more functional groups (nucleophilic functional groups or electrophilic functional groups) which are different from those in the first solution at the side chain and/or at the terminal, and a dispersion medium as essential constitutional elements. The second solution can contain cells and a cell action additive, as necessary.

There may be a plurality of kinds of second solutions. In that case, the multi-branched polymer which has functional groups different from those in the first solution and has, as the skeleton, polyethylene glycol having one or more nucleophilic functional groups or electrophilic functional groups at the side chain and/or at the terminal, the dispersion medium, the cells, and the cell action additive, which are contained in each of the second solutions, may differ overall or in part. For example, cells contained in a second solution a and cells contained in a second solution b may be the same or different from each other.

<<Gel-Forming Step>>

A "gel-forming step" is a step in which a hydrogel is formed by mixing the first solution with the second solution and performing the reaction of the respective multi-branched polymers having polyethylene glycol as the skeleton contained therein. One of the first solution and the second solution may be ejected by the liquid droplet ejection device, or both of the first solution and the second solution may be ejected by the liquid droplet ejection device.

The "liquid droplet ejection device" is means for ejecting a solution stored in a liquid chamber in the form of liquid droplets and landing the liquid droplets on the target portion. Examples of the ejection method for the ejection device include an inkjet method and a dispenser method as a gel extrusion method. In the inkjet method, a solution is ejected from an ejection hole (a nozzle). Since a fine solution (may be referred to as a liquid droplet) can be ejected from the ejection hole in the ejection method, a highly accurate three-dimensional structure can be produced.

The amount of the liquid droplet to be ejected can be any amount. Preferably, it is 9 pL or more, 15 pL or more, 20 pL or more, 30 pL or more, 40 pL or more, 50 or more, 60 pL or more, 70 pL or more, 80 pL or more, 90 pL or more, or 100 pL or more, and 900 pL or less, 800 pL or less, 700 pL or less, 600 pL or less, 500 pL or less, 400 pL or less, or 300 pL or less.

"Landing" refers to bringing a solution into contact with a target portion. This is achieved by ejecting the liquid droplets to the target portion by the ejection method. The position at which the solution is ejected is not particularly limited, and the solution may be ejected so as to be applied at the desired target position. Further, the landing portions may be separated from each other, or some of them may be in contact with each other or overlap with each other.

Since the gel is formed by a reaction of multi-branched polymers having polyethylene glycol as the skeleton, which respectively have a nucleophilic functional group and an electrophilic functional group, a hydrogel is formed by landing the second solution on the first solution. In a case where the second solution is ejected by the liquid droplet ejection device, a hydrogel can be generally formed as a dot-shaped hydrogel, which is not limited, by one landing. In the present specification, the "dot (form) shape" means a dot-like shape. Therefore, the shape is not limited to a perfect circle or a hemisphere and may be any shape such as a polygonal shape, a substantially polygonal shape, an amorphous shape, or a combination thereof, in addition to a substantially circular shape or a substantially hemispherical shape. Further, the dot (form) shape may have a predetermined length and thickness in terms of three-dimensional structure. In a case where the second solution is ejected a plurality of times, hydrogels of which the minimum unit is the dot-shaped hydrogel having various shapes are formed.

The volume of the hydrogel formed by the cross-linking reaction by one landing, that is, the volume of the dot-shaped hydrogel, depends on the number of times of the ejection of the second solution to the same location. Further, the larger the ejection hole diameter and the larger the number of times of the ejection to the same location are, the larger the volume of the dot-shaped hydrogel is. Accordingly, in a case where the number of times of ejection to the same location and the diameter of the ejection hole are changed, the volume of the dot-shaped hydrogel can be adjusted. In the present specification, the volume of the dot-shaped hydrogel is not limited; however, it is preferably 9 pL or more, 15 pL or more, 20 pL or more, 30 pL or more, 40 pL or more, 50 or more, 60 pL or more, 70 pL or more, 80 pL or more, 90 pL or more, or 100 pL or more, and 900 pL or less, 800 pL or less, 700 pL or less, 600 pL or less, 500 pL or less, 400 pL or less, or 300 pL or less. The diameter of the dot-shaped hydrogel is not limited and may be in the range of 10 μm or more and 300 μm or less, and the thickness thereof may be in the range of 5 μm or more and 150 μM or less.

Since the second solution is ejected any number of times, a plurality of dot-shaped hydrogels may be formed. Some or all of the dot-shaped hydrogels may be in contact with each other. In a case where the plurality of dot-shaped hydrogels are arranged in a row, a hydrogel having any shape as well as a dot shape may be used. The shape can be appropriately selected depending on the intended purpose. For example, in a case where the dot-shaped hydrogels are aligned in the uniaxial direction, a linear hydrogel can be formed. It is also possible to form a film-shaped (planar) hydrogel by aligning the linear hydrogels in the same plane without gaps.

<<Removal Step>>

A "removal step" is a step of removing an unreacted, that is, an uncrosslinked, multi-branched polymer present on the substrate or the hydrogel after the gel-forming step. This step is an optional step and may be performed as necessary.

The removal method is not particularly limited, and any known removal method can be used as long as it is a method that does not have a physical, biological, or chemical effect on the formed hydrogel. A simple removal method that is generally performed is a method of washing a support or a hydrogel with an appropriate washing liquid.

The washing liquid used in the washing method is not particularly limited as long as it is a solution that does not affect the hydrogel and cells. The washing liquid may be determined as appropriate in consideration of pH, osmotic pressure, and the like. Preferred examples thereof include a buffer solution and a medium.

The washing method may be a method in which the washing liquid is poured onto the support or the hydrogel or a method in which the support or the hydrogel is immersed in the washing liquid in order to reduce physical damage to the hydrogel. Washing may be performed a plurality of times in one step.

(Cell Adhesive Material)

Examples of the cell adhesive material include a protein selected from extracellular matrices. The protein selected from the extracellular matrices is the same as that described above. The cell adhesive material may be ejected by a liquid droplet ejection device and arranged on the substrate. The liquid droplet ejection device is the same as that described above.

[Neural Circuit Model]

In one embodiment, the present invention provides a neural circuit model that includes a substrate and a plurality of cell aggregates arranged on the substrate, each of the plurality of cell aggregates containing nerve cells and at least two cell aggregates being functionally connected. In the neural circuit model of the present embodiment, each of the cell aggregates preferably contains 7 to 10,000 cells.

The neural circuit model of the present embodiment can accurately reproduce in vitro the activity state of nerve cells in a living body and can be used for the elucidation of the brain function, toxicity evaluation of the nervous system-involved disease, drug discovery and drug development, or the like.

In the neural circuit model of the present embodiment, the substrate and nerve cells are the same as those described above. In addition, the functional connection between the cell aggregates is as described above and means that a nerve cell extends a protrusion called an axon, which forms a synaptic connection with a dendrite of another nerve cell. As a result, a neural circuit is formed.

In the neural circuit model of the present embodiment, the substrate may be a substrate in which a pattern of a cell non-adhesive material is arranged on the surface. In addition, the substrate may be a substrate in which a pattern of a cell adhesive material is arranged on the surface.

The arrangement pattern and the number of patterns of cell aggregates on the substrate are not particularly limited, and the pattern may be, for example, a circle shape, a rectangular shape, or a grid shape. In addition, the functional connection between the cell aggregates arranged on the substrate may be a random connection or may be a connection configured to circulate each of cell aggregates.

[Manufacturing Method for Neural Circuit Model]

In one embodiment, the present invention provides a manufacturing method for a neural circuit model including a cell culture carrier-forming step of arranging a cell adhesive material and a cell non-adhesive material on a substrate to form a microstructure for cell arrangement, a cell-arranging step of arranging nerve cells on the substrate, a step of incubating the liquid pool until the arranged nerve cells sediment and temporarily adhere onto the substrate to form a cell aggregate, a medium-adding step of supplying a medium to the substrate on which the cell aggregate is formed, and a culture step of culturing the cell aggregate to form a neural circuit model.

In the manufacturing method of the present embodiment, the substrate may be the substrate described above or may be a substrate having a non-porous flat plate member in which a porous member is laminated. Examples of the non-porous flat plate member include one formed from the substrate material described above, and more specific examples thereof include a culture dish and glass.

The porous member may be, for example, a porous membrane. The pore size of the porous member is preferably a size that does not allow cells to be buried, and for example, a pore size of 1 µm or less is preferable.

Figure 8:
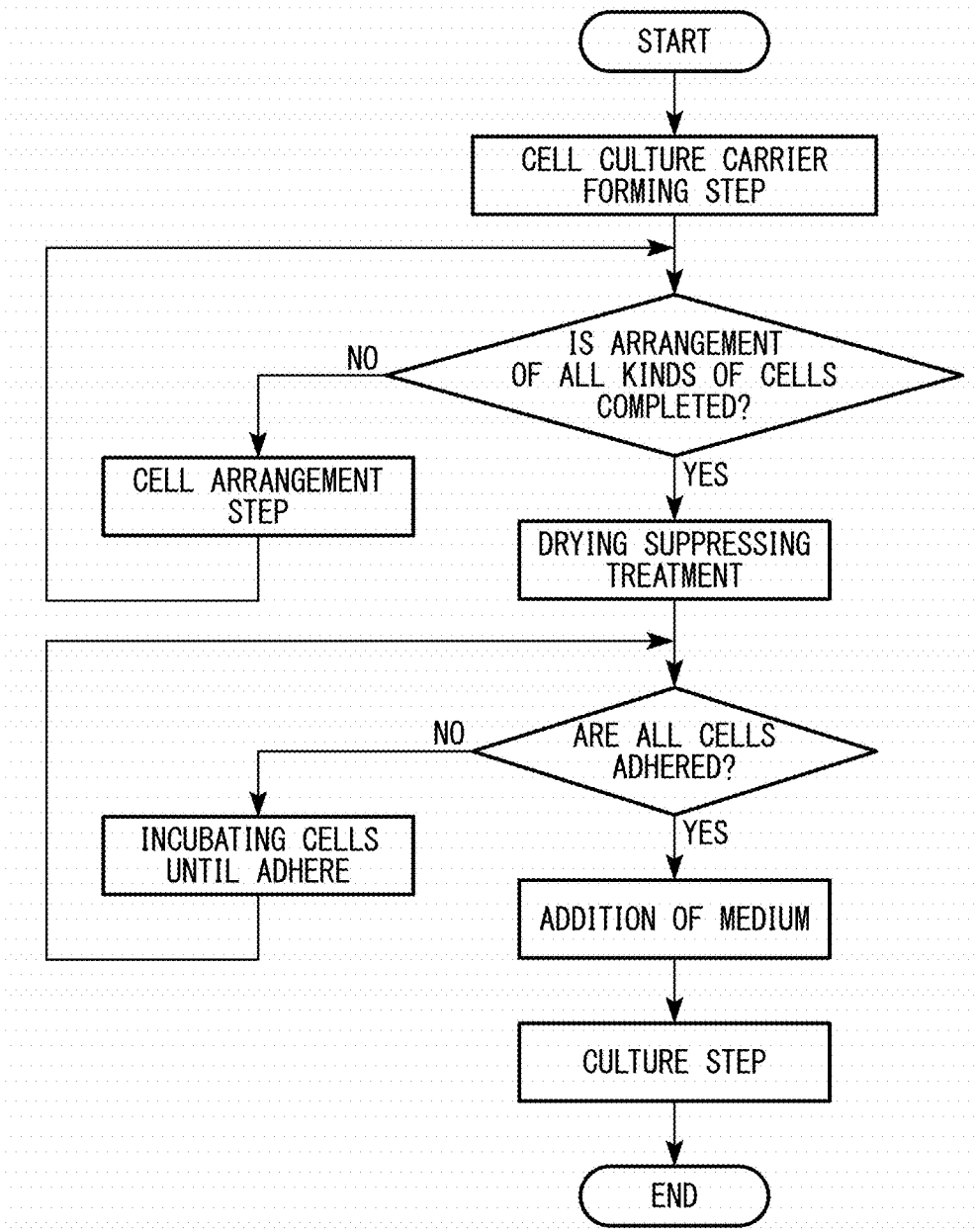
FIG. 8 is a flow chart illustrating one example of a manufacturing method for a neural circuit model.

FIG. 8 is a flow chart of the manufacturing method of the present embodiment. In the cell culture carrier-forming step, first, a cell adhesive material and a cell non-adhesive material are arranged on a substrate to form a microstructure for cell arrangement, as illustrated in FIG. 8. The cell adhesive material and the cell non-adhesive material are the same as those described above.

Subsequently, in the cell-arranging step, cells are arranged in the cell arrangement region of the microstructure for cell arrangement. It is preferable that the cells be arranged by an inkjet method. Further, in a case where a plurality of kinds of cells are arranged in the microstructure for cell arrangement, all kinds of cells are arranged in this step.

In the manufacturing method of the present embodiment, it is preferable to carry out a drying suppression treatment. For example, in a case where a substrate having a porous structure is used as the substrate and a liquid pool is formed in a state where a liquid such as a medium is retained in the substrate in advance, the liquid is retained by the above-described porous structure, and thus drying of the liquid pool can be suppressed.

Further, in a case where liquid droplets are ejected onto the dried substrate to form a liquid pool, the shape of the liquid pool can be maintained and the adhesion of the cells on the substrate can be stably achieved by carrying out a step of suppressing the evaporation of the liquid in the liquid pool (drying-suppressing step). Examples of the drying-suppressing step include the same steps as those described above. The drying suppression treatment may be carried out after the cell-arranging step or before the cell culture carrier-forming step.

Subsequently, in the incubating step, the cells were left to stand until all the cells adhered to the substrate. Subsequently, in the medium adding step, the medium is added. The medium is the same as that described above. Subsequently, in the culture step, the cell aggregate is cultured to form a neural circuit model.

Figure 9:
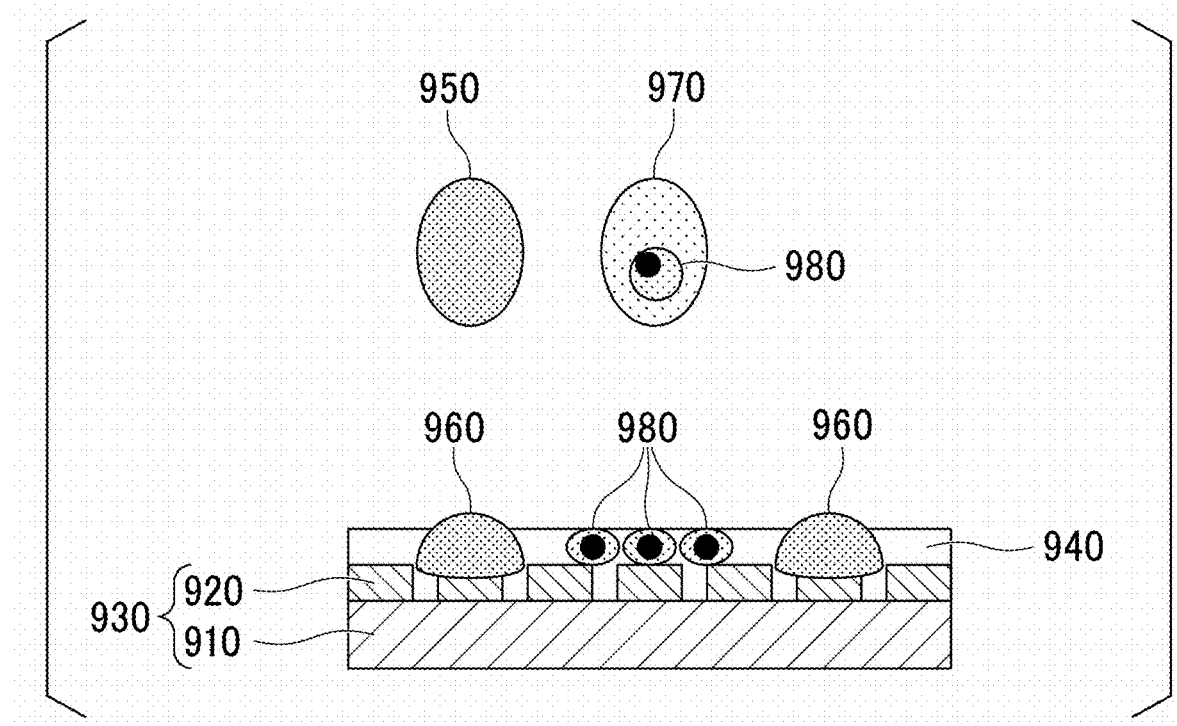
FIG. 9 is a schematic cross-sectional view illustrating a manufacturing method for a neural circuit model.

FIG. 9 is a schematic cross-sectional view illustrating a manufacturing method for a neural circuit model. As illustrated in FIG. 9, a cell culture carrier 930 is obtained by laminating a porous member 920 on a flat plate member 910.

The method for forming the microstructure for cell arrangement on the porous member is not particularly limited, but in the example of FIG. 9, the porous member 920 is immersed in the above-described first solution 940 and subsequently arranged on a flat plate member 910, and then a second solution 950 is ejected from the inkjet head.

In a case where the first solution 940 reacts with the second solution 950, a hydrogel (a Tetra-PEG gel) 960, which is a cell non-adhesive material, is formed. The reaction of the first solution 940 with the second solution 950 can be carried out, for example, by incubating the solutions to stand for 30 minutes in a high-humidity environment. Here, as the high-humidity environment, a relative humidity of 90% or more is preferable.

Subsequently, the cells are arranged. In the example of FIG. 9, cells 980 are arranged by ejecting the above-described cell ink 970 by the inkjet method. At this time, since a medium is retained in the porous member 920, the impact that is generated in a case where the fine liquid droplets of the cell ink 970 ejected land on the surface can be alleviated, and thus, damage to the cells can be reduced. Further, since a medium is retained in the porous member 920, it is possible to prevent the fine liquid droplets from drying out.

EXAMPLES

Next, the present invention will be described in more detail by way of Examples, but the present invention is not limited to the following Examples.

Experimental Example 1

(Evaluation of Cell Migration 1)

Cells were seeded on a substrate and the occurrence of migration was evaluated. As the substrate, a slide glass coated with Matrigel (registered trade mark, manufactured by Corning Incorporated) was used. As cells, PC12 cells, which are a cell line derived from rat pheochromocytoma, were used. Cell seeding was performed by an inkjet method.

<<Preparation of Cell Ink>>

First, cells were stained. A green fluorescent dye (trade name: Cell Tracker Green, manufactured by Thermo Fisher Scientific, Inc.) was dissolved in dimethyl sulfoxide (DMSO) at a concentration of 10 mmol/L (mM) and mixed with a medium, thereby preparing a medium containing the green fluorescent dye of a concentration of 10 µmol/L (µM).

Subsequently, 5 mL of a serum-free medium containing the green fluorescent dye was added to the dish of the cultured PC12 cells, and the cells were cultured in an incubator (KM-CC17RU2, manufactured by Panasonic Corporation, in an environment of 37° C. and 5% by volume $CO_2$) for 30 minutes. Thereafter, the cells were detached from the dish by trypsin treatment to obtain a cell suspension. Subsequently, some of the cell suspension was placed on a plastic slide made of PMMA, and the number of cells was counted using a Countess (trade name) Automated Cell Counter (manufactured by Thermo Fisher Scientific, Inc.).

As the dispersion medium for cell ink, PBS (−) supplemented with 0.5% by mass of glycerin (molecular biology grade, manufactured by FUJIFILM Wako Pure Chemical Corporation) as a cell-drying inhibitor was used. PC12 cells were dispersed in the dispersion medium such that the concentration thereof was $6 \times 10^6$ cells/mL, thereby obtaining a cell ink.

<<Cell Ejection>>

Figure 4:
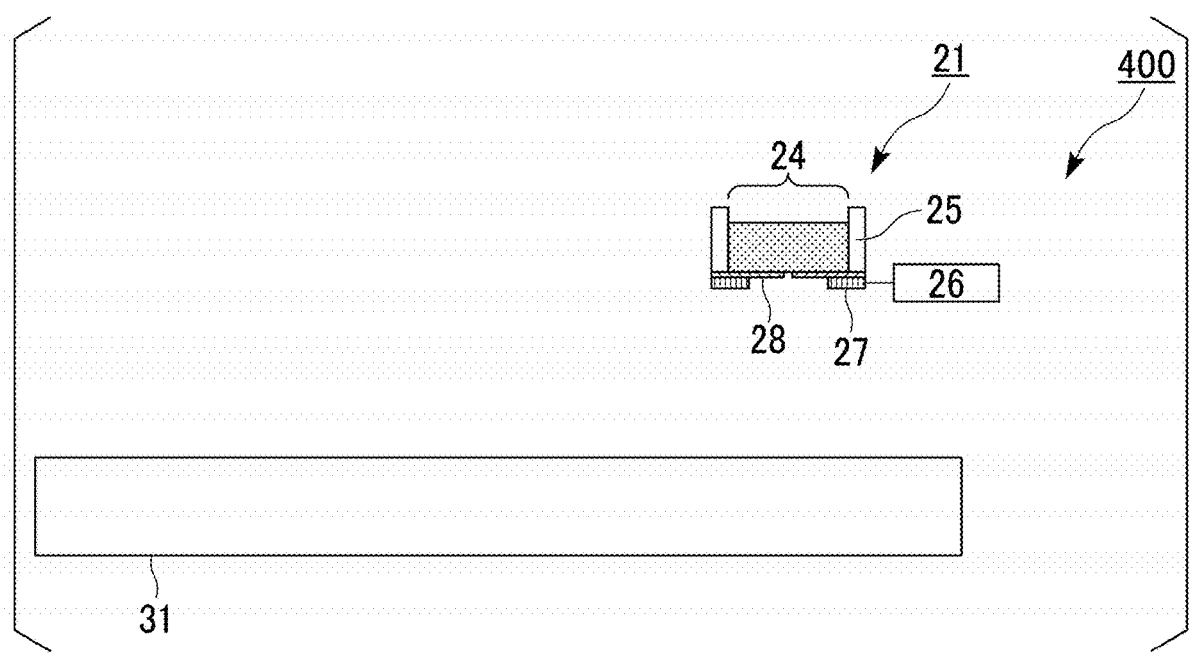
FIG. 4 is a schematic view illustrating one example of a liquid droplet-arranging device.

The liquid chamber of the cell ejection head of the device in FIG. 4 was filled with a cell ink. Subsequently, liquid droplets of the cell ink were ejected onto the substrate, and liquid pools were arranged. The diameter per one liquid pool was about 200 µm. In addition, the liquid pools arranged on the substrate contained about 100 cells per one liquid pool, and the cell density in the liquid pool was $3 \times 10^5$ cells/cm². The density in the liquid pool refers to the number of cells per area in which the liquid pools arranged on the substrate are in contact with the substrate.

Figure 10A:
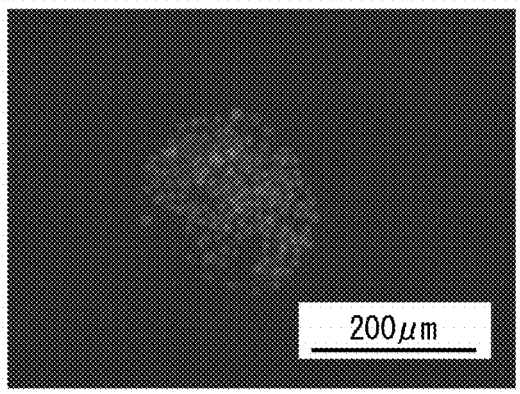
FIGS. 10A to 10C are photomicrographs taken in Experimental Example 1.
Figure 10B:
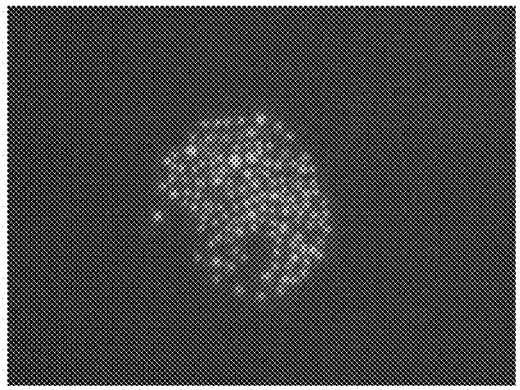

FIG. 10A is a photomicrograph taken immediately after ejecting the cell ink. In a case where the cells were left to stand in a high-humidity environment of a relative humidity of 95% or more for about 10 minutes after the liquid droplets of the cell ink were applied, the cells in the liquid droplets sedimented and temporarily adhered onto the substrate to form a cell aggregate. Subsequently, a medium was added gently. FIG. 10B is a photomicrograph taken immediately after adding the medium.

<<Cell Culture>>

Figure 10C:
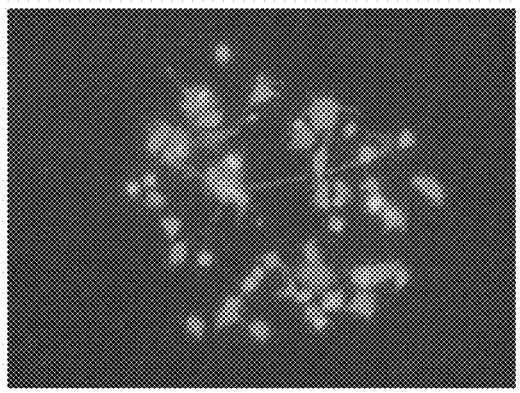

Subsequently, the cells were cultured in an incubator for 1 day in an environment of 37° C. and 5% by volume $CO_2$. FIG. 10C is a fluorescence photomicrograph that shows the observation result of the fluorescence of Cell Tracker Green in cells one day after the start of culture. From the result, it was revealed that the cells migrate and move from the position immediately after the ejection. In a case where such migration occurs, it is difficult to cause the cells to remain in the predetermined position.

Experimental Example 2

(Evaluation of Cell Migration 2)

The number of cells in the liquid pool was changed and the cells were seeded on the substrate, and then the occurrence of migration was evaluated. As the substrate, a slide glass coated with Matrigel (registered trade mark) was used. As the cells, PC12 cells were used. Cell seeding was performed by an inkjet method.

The cell ink production and the cell ejection were carried out in the same manner as in Experimental Example 1. However, the number of cells in the liquid pool was changed in the cell ejection. Specifically, 1 or more and less than 3 cells (cell density: $2 \times 10^4$ cells/cm$^2$), 3 to 6 cells (cell density: $6 \times 10^4$ cells/cm$^2$), or 7 to 11 cells (cell density: $1 \times 10^5$ cells/cm$^2$) were arranged per one liquid pool arranged on the substrate. Here, density refers to the number of cells per area in which the liquid pools arranged on the substrate are in contact with the substrate. The diameter per one liquid pool was about 100 μm.

Figure 11:
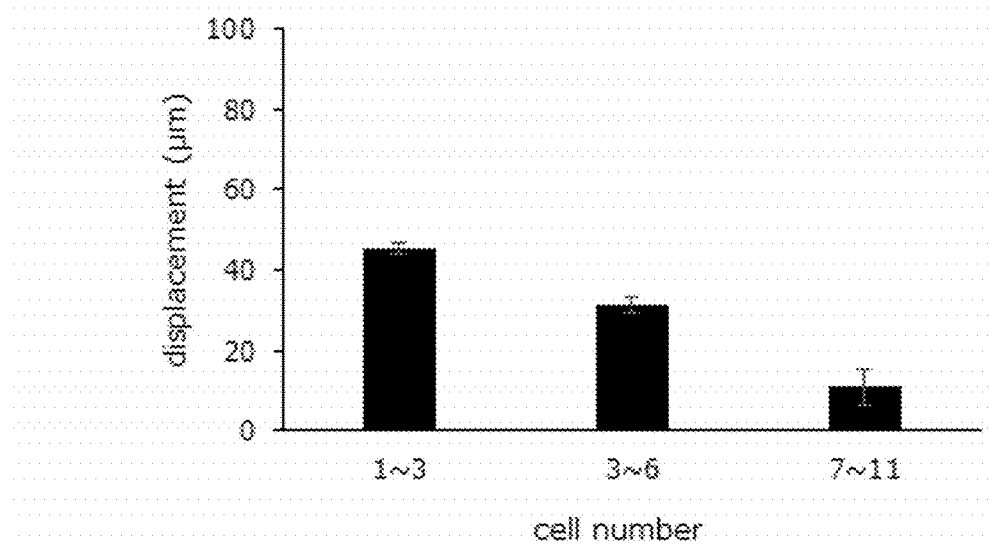
FIG. 11 is a graph showing the results of Experimental Example 2.

Subsequently, the cells were cultured in an incubator for 1 day in an environment of 37° C. and 5% by volume $CO_2$, and individual cells were observed over time using an inverted microscope (model "CKX41", manufactured by Olympus Corporation) to measure the migration distance of each cell. FIG. 11 is a graph showing the measurement results of the migration distance of cells one day after the start of culture. The vertical axis of the graph indicates the migration distance (displacement) (μm).

As a result, it was revealed that in a case where the number of cells per one liquid pool is 7 or more and the cell density in the liquid pool is $10^5$ cells/cm$^2$ or more, cell migration is suppressed.

Experimental Example 3

(Nerve Cell Pattern Control)

A pattern of the cell non-adhesive material and a pattern of the cell adhesive material were arranged on the substrate. As a substrate, a slide glass was used on which a porous culture membrane (trade name: ipCELLCULTURE Track Etched Membrane, pore size: 0.45 μm, pore density: $4 \times 10^6$ pores/cm$^2$, thickness: 12 μm, manufactured by it4ip S.A.) having a diameter of 13 mm and made of polyester was laminated.

Figure 12:
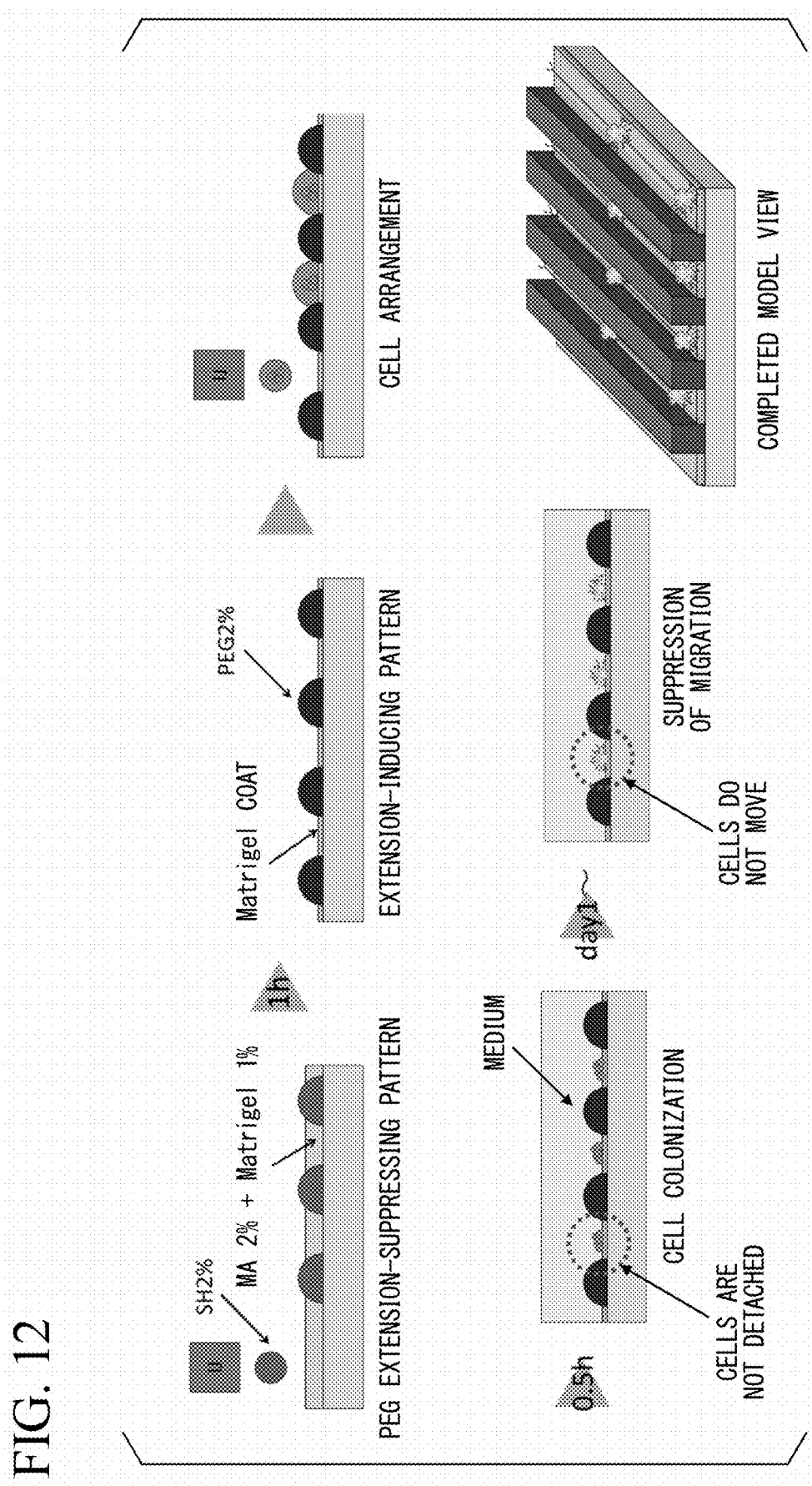
FIG. 12 is a schematic view illustrating a procedure for arranging a pattern of a cell non-adhesive material and a pattern of a cell adhesive material on a substrate and the arrangement of cells.

Subsequently, nerve cells were seeded on this substrate, and axon extension was observed. As the nerve cells, GABAergic nerve cells derived from human iPS cells (manufactured by Elixirgen Scientific, Inc.) were used. FIG. 12 is a schematic view illustrating a procedure for arranging a pattern of a cell non-adhesive material and a pattern of a cell adhesive material on a substrate and the arrangement of cells.

<<Preparation of First Solution>>

Tetra-PEG-SH (trade name "SUNBRIGHT PTE-100SH", manufactured by Yuka Sangyo Co., Ltd.) was dissolved in PBS (−), and then filtered through a filter (trade name "Minisart Syringe Filter 175497K", manufactured by Sartorius AG) having an average pore size of 0.2 μm to obtain the first solution containing 2% Tetra-PEG-SH.

<<Preparation of Second Solution>>

Tetra-PEG-maleimidyl (trade name "SUNBRIGHT PTE-100MA", manufactured by Yuka Sangyo Co., Ltd.) and Matrigel (registered trade mark, manufactured by Corning Incorporated) were dissolved in PBS (−) and filtered through a filter having an average pore size of 0.2 μm to obtain the second solution containing 2% Tetra-PEG-maleimidyl and 1% Matrigel was prepared.

<<Pattern Formation>>

The substrate was immersed in the first solution and taken out, and a liquid phase of the first solution was formed on the substrate. Subsequently, the liquid chamber of the inkjet head was filled with the second solution, and the second solution was added drop wise onto the substrate to form a linear pattern having a width of about 200 μm. As a result, Tetra-PEG-SH contained in the first solution and Tetra-PEG-maleimidyl contained in the second solution were cross-linked to form a hydrogel pattern. This hydrogel is a cell non-adhesive material. In addition, a pattern of the cell adhesive material was formed in the portion coated with Matrigel (registered trade mark). Subsequently, the substrate was immersed in phosphate buffered saline (manufactured by Thermo Fisher Scientific, Inc., hereinafter also referred to as PBS (−)) to remove excess first solution and second solution.

<<Preparation of Cell Ink>>

The cell ink was prepared in the same manner as in Experimental Example 1 except that GABAergic nerve cells derived from human iPS cells (manufactured by Elixirgen Scientific, Inc.) were used as cells.

<<Cell Ejection>>

The liquid chamber of the cell ejection head of the device in FIG. 1 was filled with the cell ink. Subsequently, liquid droplets of the cell ink were ejected onto the pattern of the cell adhesive material on the substrate, and liquid pools were arranged.

In a case where the cells were left to stand for about 30 minutes after the liquid droplets of the cell ink were applied, the cells in the liquid droplets sedimented and temporarily adhered onto the substrate to form a cell aggregate. Subsequently, a medium was added gently.

<<Cell Culture>>

Figure 13A:
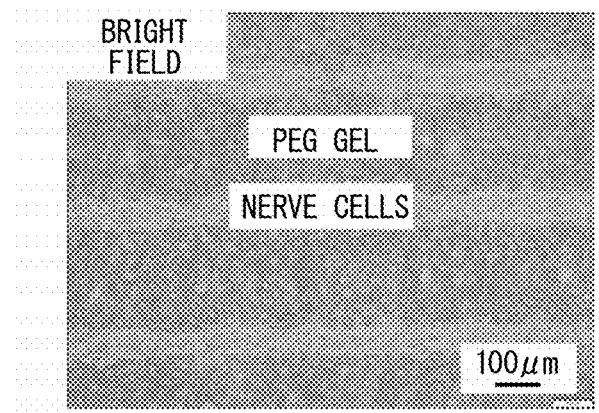
FIGS. 13A to 13D are photomicrographs taken in Experimental Example 3.
Figure 13B:
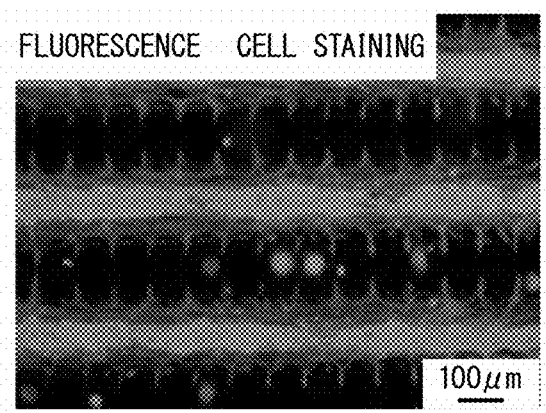
Figure 13C:
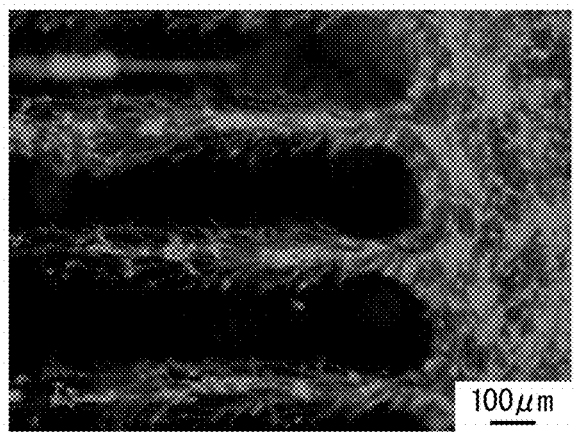
Figure 13D:
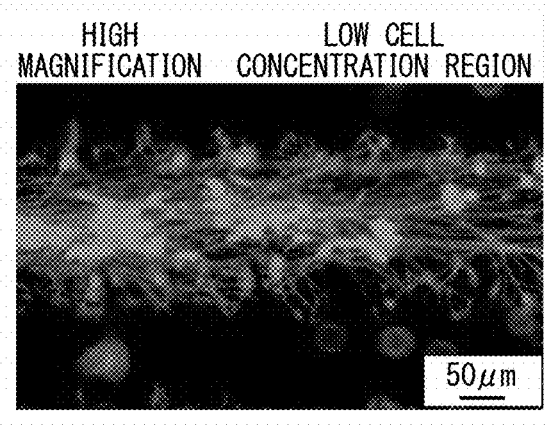

Subsequently, the cells were cultured in an incubator in an environment of 37° C. and 5% by volume $CO_2$. FIG. 13A is a bright-field photomicrograph of cells observed 4 days after the start of culture. The length of the scale bar is 100 μm. FIGS. 13B and 13C are fluorescence photomicrographs that show the observation results of the fluorescence of Cell Tracker Green on the substrate. The length of the scale bar is 100 μm. FIG. 13D is a fluorescence photomicrograph that shows the observation result of the fluorescence of Cell Tracker Green in the region in which the cell density is low. The length of the scale bar is 50 μm.

As a result, it was revealed that the cells do not migrate to the region in which the pattern of the cell non-adhesive material was arranged. It was also revealed that the axons are formed only in the region excluding the pattern of the cell non-adhesive material. From the above results, it was revealed that in a case where a pattern of the cell non-adhesive material is arranged on the substrate, the axon extension of the nerve cell can be controlled.

Experimental Example 4

(Nerve Cell Non-Pattern Control)

A substrate having only the cell adhesive material was produced by the same method as in Experimental Example 3. Subsequently, liquid droplets of the cell ink were ejected onto the pattern of the cell adhesive material on the substrate in the same manner as in Experimental Example 3, and nerve cells were seeded. As the nerve cells, GABAergic nerve cells derived from human iPS cells (manufactured by Elixirgen Scientific, Inc.) were used.

Subsequently, the cells were cultured in an incubator in an environment of 37° C. and 5% by volume $CO_2$, and the axon extension of nerve cells was checked 7 days after the start of the culture. Specifically, first, Calcein-AM (Thermo Fisher Scientific, Inc.) diluted with DMSO was added to the medium so that the final concentration was 10 μM, and incubated for 30 minutes in an environment of 37° C. and 5% by volume $CO_2$. Subsequently, the nerve cells were observed under a fluorescence microscope.

Figure 14:
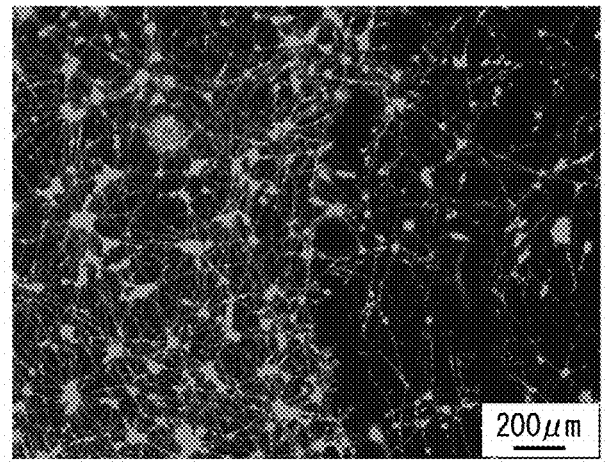
FIG. 14 is a fluorescence photomicrograph taken in Experimental Example 4.

FIG. 14 is a fluorescence photomicrograph of the nerve cells. The length of the scale bar is 200 μm. From the above results, it was confirmed that in a case where the pattern of the cell non-adhesive material is not arranged on the substrate, the direction of the axon extension of the nerve cell is not controlled.

Experimental Example 5

(Production of Neural Circuit Model 1)

The diameter of the liquid pool on the substrate, the cell density in the liquid pool, the number of cells per one liquid pool, the size of the pattern of the cell non-adhesive material, and the size of the pattern of the cell adhesive material were changed variously according to the combinations shown in Table 1 below to produce neural circuit models, which were subsequently evaluated. A 10-cm dish was used as the substrate. As the nerve cells, GABAergic nerve cells derived from human iPS cells (manufactured by Elixirgen Scientific, Inc.) were used.

FIGS. 15A to 15E are schematic views illustrating a procedure of this Experimental Example. FIGS. 15A to 15D are side views, and FIG. 15E is a top view of FIG. 15B. As illustrated in FIGS. 15A to 15E, the cell adhesive material was arranged in a circle form to form a cell adhesive portion. In addition, the cell non-adhesive material was arranged to surround the cell adhesive portion to form a cell non-adhesive portion. The shape of the cell non-adhesive portion was substantially a donut shape, which was concentric with the cell adhesive material.

FIG. 15A is a schematic view illustrating a step of arranging liquid droplets containing nerve cells on a substrate. FIG. 15B is a schematic view illustrating a state in which a plurality of liquid droplets land on the substrate to form a liquid pool. The end portion of the liquid pool may be located on the cell non-adhesive portion and is preferably located so as not to cross the cell non-adhesive portion. FIG. 15C is a schematic view illustrating a state in which nerve cells in the liquid pool have sedimented and temporarily adhered onto the substrate to form a cell aggregate. FIG. 15D is a schematic view illustrating a step of supplying a medium to the substrate on which the cell aggregate is formed.

In Table 1, "Diameter of liquid pool" indicates the diameter of the liquid pool arranged on the substrate, "Cell density" indicates the cell density in the liquid pool, "Number of cells" indicates the number of cells per one liquid pool, "Inner diameter/outer diameter of non-adhesive portion" indicates the inner diameter and outer diameter of the donut-shaped portion of the cell non-adhesive portion, "Diameter of adhesive portion" indicates the diameter of the cell adhesive portion, and "Cell arrangement method" indicates whether the cells are arranged by the inkjet method (IJ) or by a manual procedure. The "Cell density" was defined as the number of cells per area in which the liquid pools arranged on the substrate were in contact with the cell adhesive portion. "N. D." indicates that measurement was not possible.

The pattern of the cell non-adhesive material was formed in the same manner as in Experimental Example 3, by crosslinking Tetra-PEG-SH contained in the first solution and Tetra-PEG-maleimidyl contained in the second solution. In addition, in a case of forming a pattern of the cell adhesive material, the liquid chamber of the inkjet head was filled with Matrigel (registered trade mark, Corning Incorporated) and then Matrigel was ejected pattern-wise.

The following evaluation items of the neural circuit model were evaluated: the diameter of the liquid pool, the initial arrangement of cells, and the fixation of cells. Table 1 also shows the results of these evaluation items.

The goal was to control the diameter of the liquid pool to 500 μm or less, but this goal was difficult to achieve by a manual procedure. In the arrangement of cells by the inkjet method, it was possible to control the diameter of the liquid pool to be more than 500 μm or to be 500 μm or less.

The evaluation criteria for the initial arrangement of cells were as follows.
 −: Cells were randomly arranged.
 +: A discrete pattern of cells was formed.

The evaluation criteria for cell fixation were as follows, and cell migration was evaluated on day 1 to day 7 of the culture.
 −: The cells migrated outside the liquid droplets arranged on the substrate or were randomly arranged.
 +: The cells remained inside the liquid droplets arranged on the substrate.

TABLE 1

| | Example 1 | Example 2 | Example 3 | Example 4 | Example 5 | Example 6 | Comparative Example 1 | Comparative Example 2 | Comparative Example 3 | Comparative Example 4 | Comparative Example 5 | Comparative Example 6 |
|---|---|---|---|---|---|---|---|---|---|---|---|---|
| Diameter of liquid pool (μm) | 500 | 300 | 300 | 200 | 300 | 400 | 1,200 | 1,200 | 1,200 | 1,200 | 400 | 700 |
| Cell density (cells/cm$^2$) | $1 \times 10^5$ | $1 \times 10^5$ | $1 \times 10^5$ | $1 \times 10^5$ | $1 \times 10^5$ | $1 \times 10^5$ | $1 \times 10^5$ | $1 \times 10^6$ | N. D. | $7 \times 10^4$ | $7 \times 10^4$ | $5 \times 10^4$ |
| Number of cells (cells) | 32 | 32 | 315 | 7 | 70 | 70 | 1,000 | 5,000 | 1,000 | 1,000 | 50 | 50 |
| Inner diameter/outer diameter of non-adhesive portion (μm) | 300/600 | 200/500 | 200/500 | 100/400 | 400/700 | 300/600 | 1,000/1,500 | 1,000/1,500 | Without non-adhesive portion | Without non-adhesive portion | 300/600 | 300/600 |

TABLE 1-continued

|  | Example 1 | Example 2 | Example 3 | Example 4 | Example 5 | Example 6 | Comparative Example 1 | Comparative Example 2 | Comparative Example 3 | Comparative Example 4 | Comparative Example 5 | Comparative Example 6 |
|---|---|---|---|---|---|---|---|---|---|---|---|---|
| Diameter of adhesive portion (μm) | 400 | 200 | 200 | 100 | 300 | 300 | 1,000 | 1,000 | Without adhesive portion | 1,000 | 300 | 300 |
| Cell arrangement method | IJ | IJ | IJ | IJ | IJ | IJ | Manual procedure | Manual procedure | Manual procedure | Manual procedure | IJ | IJ |
| Initial arrangement of cells | + | + | + | + | + | + | + | + | + | + | + | + |
| Fixation of cells | + | + | + | + | + | + | + | + | − | − | − | − |

As a result, in the neural circuit models of Examples 1 to 6, good evaluation results were obtained in the evaluation items of the diameter of the liquid pool, the initial arrangement of cells, and the fixation of cells. On the other hand, in the neural circuit models of Comparative Examples 1 to 6, the diameter of the liquid pool exceeded 500 μm, or the evaluation result of any one of the evaluation items was poor.

From these results, it was revealed that in a case where the liquid droplet arranged on the substrate includes 7 or more cells per one liquid droplet and the cell density in the liquid droplet is $10^5$ cells/cm$^2$ or more, cells can be stably arranged on the substrate even in a case where the diameter per one liquid pool is 500 μm or less.

Experimental Example 6

(Production of Neural Circuit Model 2)

Figures 16A, 16B:
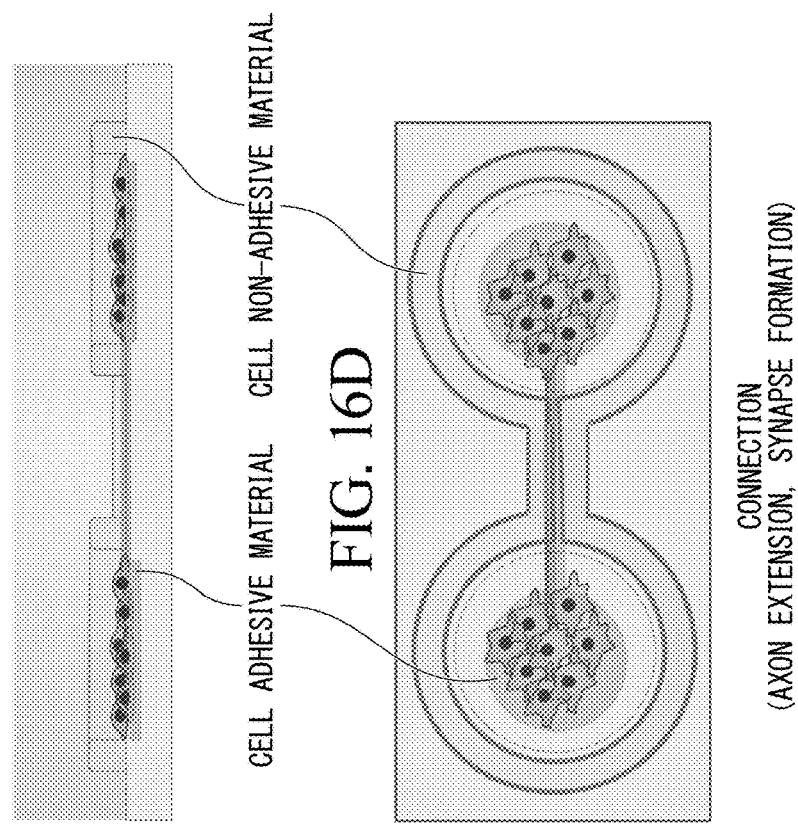
FIGS. 16A to 16D are schematic views illustrating the arrangement of cells in Experimental Example 6.
Figures 16C, 16D:
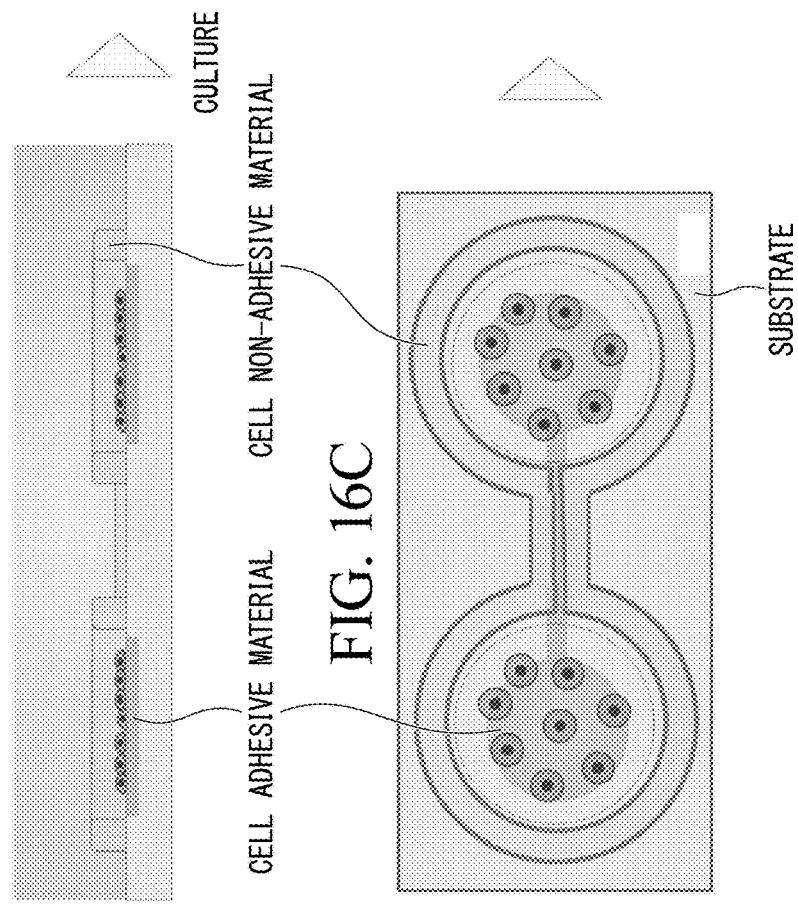

FIGS. 16A to 16D are schematic views illustrating the arrangement of cells in the neural circuit model of the experimental example in which both the cell non-adhesive material and the cell adhesive material are arranged. FIGS. 16A to 16B are side views, and FIGS. 16C and 16D are top views. FIGS. 16A and 16C illustrate a state immediately after cells are arranged, and FIGS. 16B and 16D illustrate a state where an axon is extended between cell aggregates and a synapse is formed after cell culture.

In this experimental example, a neural circuit model illustrated in FIGS. 16A to 16D was produced. The pattern of the cell non-adhesive material was formed in the same manner as in Experimental Example 3, by crosslinking Tetra-PEG-SH contained in the first solution and Tetra-PEG-maleimidyl contained in the second solution. In addition, in a case of forming a pattern of the cell adhesive material, the liquid chamber of the inkjet head was filled with Matrigel (registered trade mark, Corning Incorporated) and then Matrigel was ejected pattern-wise. A 10-cm dish was used as the substrate. As the nerve cells, GABAergic nerve cells derived from human iPS cells (manufactured by Elixirgen Scientific, Inc.) were used. As a result, a neural circuit model was obtained.

Experimental Example 7

(Production of Neural Circuit Model 3)

Figure 17A:
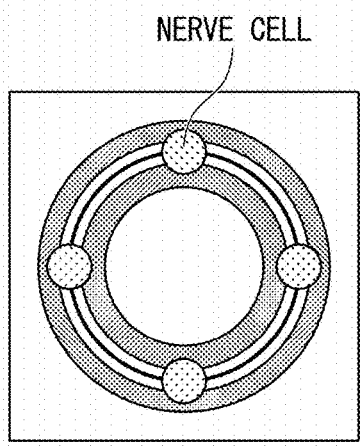
FIG. 17A is a schematic view illustrating an arrangement pattern of a cell non-adhesive material and nerve cells in a neural circuit model produced in Experimental Example 7.

As illustrated in FIG. 17A, nerve cells were arranged in the pattern illustrated in FIG. 17A on a substrate on which the cell non-adhesive material was arranged in the shape of two concentric circles, whereby a neural circuit model was produced. The pattern of the cell non-adhesive material was formed in the same manner as in Experimental Example 3, by crosslinking Tetra-PEG-SH contained in the first solution and Tetra-PEG-maleimidyl contained in the second solution. As the nerve cells, GABAergic nerve cells derived from human iPS cells (manufactured by Elixirgen Scientific, Inc.) were used.

Figure 17B:
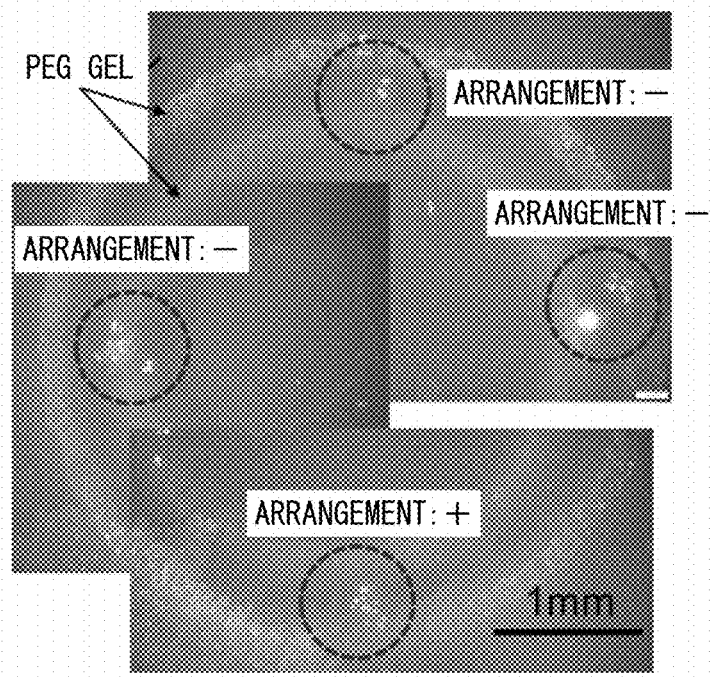
FIG. 17B is a representative photomicrograph of a neural circuit model immediately after ejecting a cell ink in Experimental Example 7.

FIG. 17B is a representative photomicrograph of a neural circuit model immediately after ejecting cell ink. In FIG. 17B, "Arrangement: +" indicates that the initial arrangement of cells was good, and "Arrangement: −" indicates that the initial arrangement of cells was poor.

Figure 18:
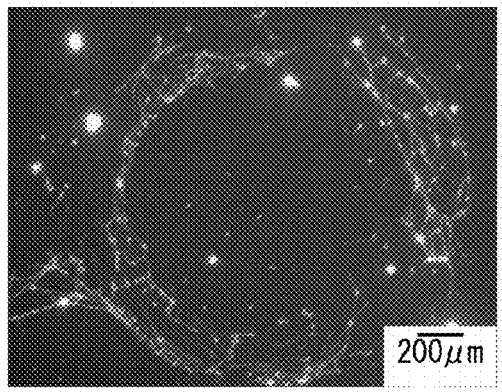
FIG. 18 is a fluorescence photomicrograph of a neural circuit model produced in Experimental Example 7.

After arranging the cells under the conditions that allowed good initial arrangement, the cells were cultured for 4 weeks, and the axon was allowed to be extended, thereby obtaining a neural circuit model. FIG. 18 is a fluorescence photomicrograph that shows the observation result of the fluorescence of Cell Tracker Green of the neural circuit model.

Experimental Example 8

(Production of Neural Circuit Model 4)

Figure 19A:
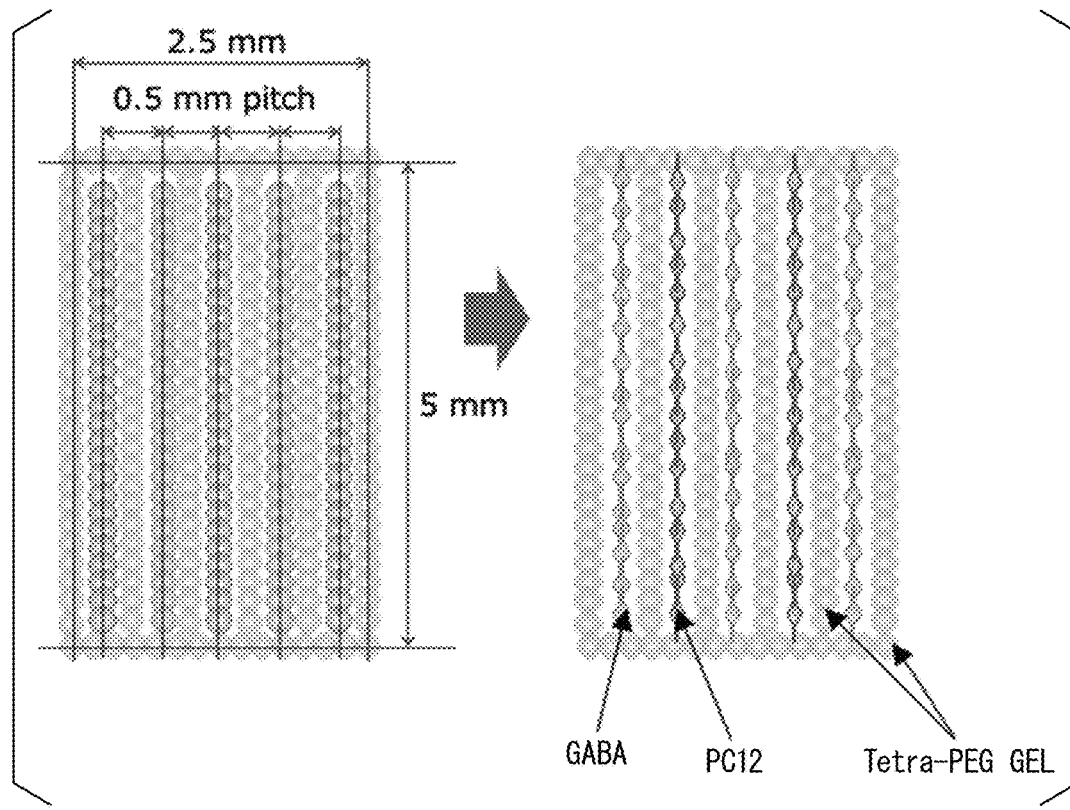
FIGS. 19A and 19B are views illustrating a pattern of a cell non-adhesive material arranged on a substrate in Experimental Example 8.
Figure 19B:
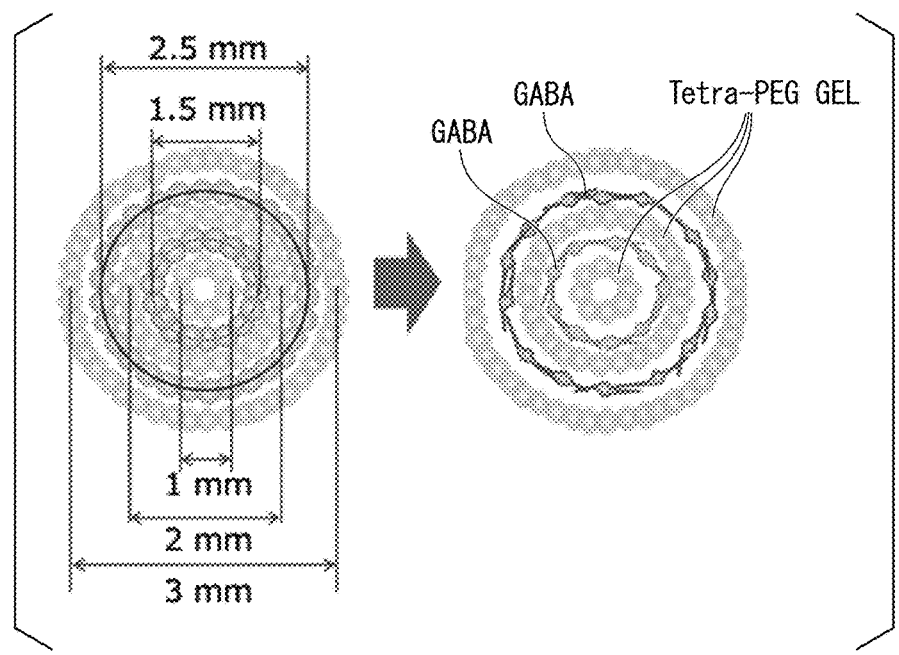

As illustrated in FIGS. 19A and 19B, a cell non-adhesive material (a Tetra-PEG gel) was arranged on the substrate.

As a substrate, a slide glass was used on which a porous culture membrane (trade name: ipCELLCULTURE Track Etched Membrane, pore size: 0.45 μm, pore density: 4×10$^6$ pores/cm$^2$, thickness: 12 μm, manufactured by it4ip S.A.) having a diameter of 13 mm and made of polyester was laminated and which was immersed in the first solution, which was the same as that in Experimental Example 3.

Subsequently, the liquid chamber of the inkjet head was filled with the second solution, which was the same as that in Experimental Example 3, and the second solution was added dropwise onto the substrate to form each of the patterns having a width of about 200 μm, which was illustrated in FIGS. 19A and 19B.

In the pattern illustrated in FIG. 19A, the pattern was formed to have a pattern shape having six straight lines. The distance between these straight lines was about 0.5 mm. The length of the straight line was about 5 mm. In the pattern illustrated in FIG. 19B, the pattern was formed to have a pattern shape having three concentric circles. The diameters of the concentric circles of the pattern were each about 1 mm, about 2 mm, and about 3 mm, from the center to the outside.

Subsequently, two kinds of nerve cells were respectively arranged in the patterns illustrated in FIGS. 19A and 19B, to produce a neural circuit model. As the nerve cells, GABAergic nerve cells derived from human iPS cells (manufactured by Elixirgen Scientific, Inc.) and pC12 cells were used.

After arranging the cells under conditions that allowed good initial arrangement, the cells were cultured for one week, and the neurite was allowed to be extended, thereby obtaining a neural circuit model. Subsequently, the neural circuit model was analyzed by immunostaining.

First, each of the obtained neural circuit models was washed with PBS and fixed with 4% paraformaldehyde (FUJIFILM Wako Pure Chemical Corporation) at 4° C. for 30 minutes. After fixation, the above sample was washed once with PBS and blocked with 1% bovine serum albumin (Thermo Fisher Scientific, Inc.) at room temperature for 20 minutes. After blocking, the sample was washed once with PBS, and a mixture of anti-βIII tubulin antibody (Sigma-Aldrich Co., LLC) and anti-tyrosine hydroxylase antibody (Abcam plc), each of which was diluted 200-fold with PBS, was added thereto as primary antibodies and then incubated overnight at 4° C.

Subsequently, the sample was washed three times with PBS, and a mixture of APC-labeled goat anti-mouse IgG (H+L) antibody (Thermo Fisher Scientific, Inc.) and Alexafluoro 594-labeled goat anti-rabbit IgG (H+L) antibody (Thermo Fisher Scientific, Inc.), each of which was diluted 500-fold with PBS, was added thereto as secondary antibodies, incubated at room temperature for 1 hour, and then washed twice with PBS.

Subsequently, a cover glass was placed on the sample, sealing was performed using a sealing solution (product name "ProLong Diamond Antifade Mountain", Thermo Fisher Scientific, Inc.), and the sealed sample was observed under a fluorescence microscope.

Figure 20A:
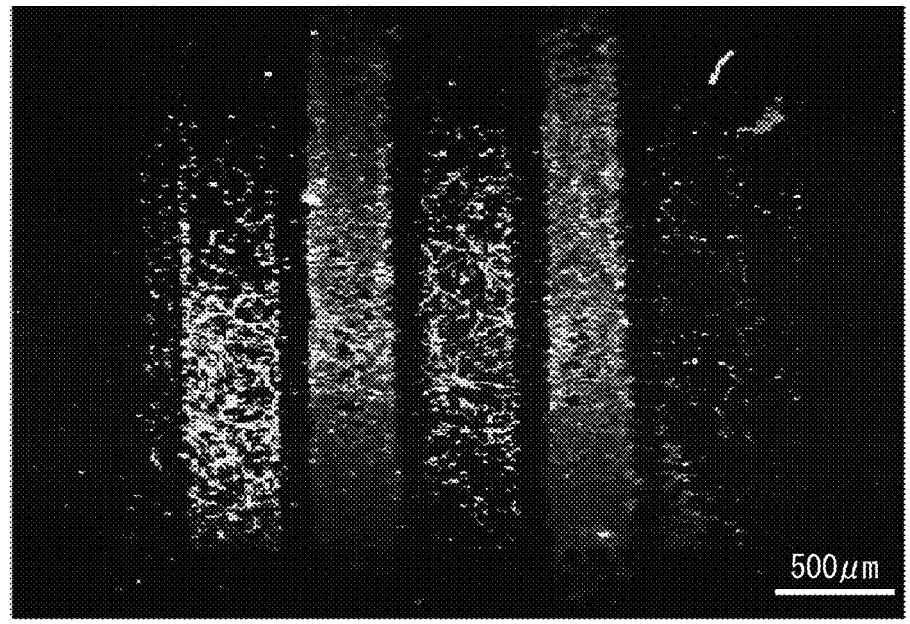
FIGS. 20A and 20B are fluorescence photomicrographs taken in Experimental Example 8.
Figure 20B:
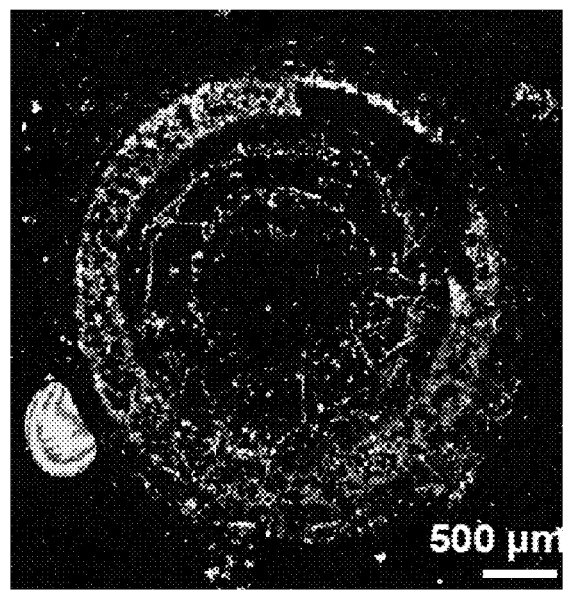

FIGS. 20A and 20B are fluorescence photomicrographs that show the observation results of the fluorescence of βIII tubulin, which is a neural skeleton of the obtained neural circuit model, and the fluorescence of tyrosine hydroxylase, which is expressed only in PC12 cells. FIG. 20A is a fluorescence photomicrograph of a neural circuit model in which nerve cells were arranged in the pattern illustrated in FIG. 19A, and FIG. 20B is a fluorescence photomicrograph of a neural circuit model in which nerve cells were arranged in the pattern illustrated in FIG. 19B.

As a result, the fluorescence of βIII tubulin was observed in the entire cell arrangement region in the neural circuit model in which the nerve cells were arranged in any pattern. It was also confirmed that the neurite grows. In addition, it was confirmed that the fluorescence of tyrosine hydroxylase was observed only in the region in which PC12 cells are arranged and the pattern of the cell arrangement was maintained.

Experimental Example 9

(Improvement of Drying Suppression Step)

Cells were seeded on a dried substrate, and the suppression of drying of the liquid pool and the occurrence of cell colonization were evaluated. A slide glass was used as the substrate. As cells, PC12 cells, which are a cell line derived from rat pheochromocytoma, were used. Cell seeding was performed by an inkjet method.

<<Preparation of Cell Ink>>

5 mL of a serum-free medium containing the green fluorescent dye was added to the dish of the cultured PC12 cells, and the cells were cultured in an incubator (KM-CC17RU2, manufactured by Panasonic Corporation, in an environment of 37° C. and 5% by volume $CO_2$) for 30 minutes. Thereafter, the cells were detached from the dish by trypsin treatment to obtain a cell suspension. Subsequently, the number of cells was measured using Nucleo Counter NC-3000 (trade name, manufactured by ChemoMetec) using some of the cell suspension.

As the dispersion medium for cell ink, PBS (−) supplemented with 0.5% by mass of glycerin (molecular biology grade, manufactured by FUJIFILM Wako Pure Chemical Corporation) as a cell-drying inhibitor was used. PC12 cells were dispersed in the dispersion medium such that the concentration thereof was $3\times10^6$ cells/mL, thereby obtaining the cell ink.

<<Cell Ejection>>

The liquid chamber of the cell ejection head of the device in FIG. 4 was filled with the cell ink. Subsequently, liquid droplets of the cell ink were ejected onto the substrate, and liquid pools were arranged. The diameter per one liquid pool was about 400 μm. In addition, the liquid pools arranged on the substrate contained about 100 cells per one liquid pool, and the cell density in the liquid pool was $8\times10^4$ cells/cm$^2$.

Figure 21A:
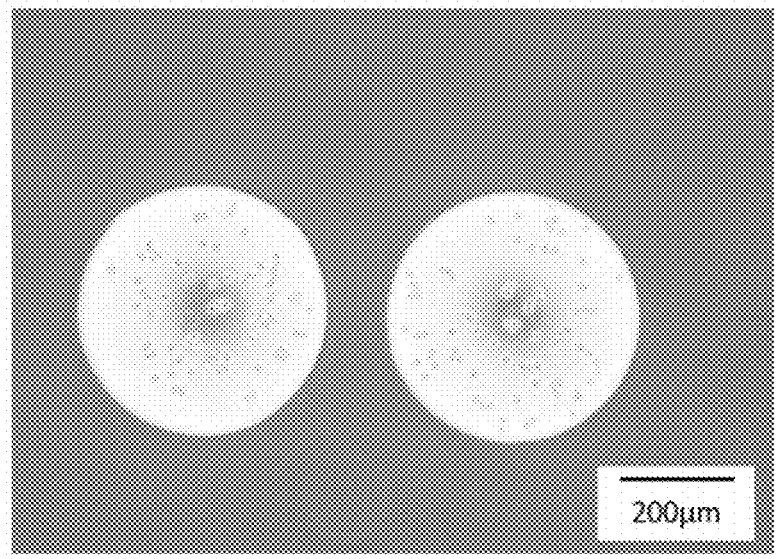
FIGS. 21A and 21B are photomicrographs taken in Experimental Example 9.

FIG. 21A is a photomicrograph of a liquid pool coated with biocompatible oil (Oil for Embryo Culture, manufactured by Fujifilm Wako Pure Chemical Corporation) immediately after the cell ink was ejected and prevented from drying. Even in a case of leaving to stand at 37° C. for 60 minutes, a small amount of liquid pool did not dry when being coated with oil, and the cells in the liquid droplet sedimented and could temporarily adhere onto the substrate to form a cell aggregate. This method can be applied not only to PC12 cells but also to many kinds of cells.

Figure 21B:
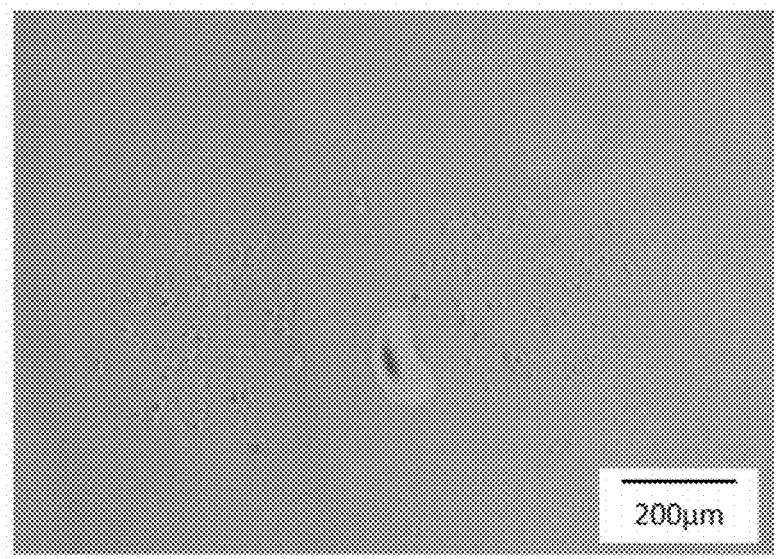

Then, the oil was gently removed, and a medium was gently added. FIG. 21B is a photomicrograph taken immediately after adding the medium. Since the amount of the liquid pool is very small, the liquid pool dries in a few minutes in a normal laboratory environment, and the volume of the liquid pool is reduced by 90% or more.

It was confirmed that cell sedimentation and temporary adhesion can be stably performed by a method of coating a liquid pool with oil or the like even in a case where a dried substrate is used, in addition to the method for incubating cells to stand in a high-humidity environment as in Experimental Examples 1 and 2 and the method for forming a liquid pool on a wetted substrate as in Experimental Examples 3 to 8.

Subsequently, the number of cells per one liquid pool and the presence or absence of the drying suppression treatment for the liquid pool on the dried substrate were changed variously according to the combinations shown in Table 2 below to produce each neural circuit model of Reference Examples 1 to 4, which was subsequently evaluated. A 35 mm dish was used as the substrate. As the nerve cells, GABAergic nerve cells derived from human iPS cells (manufactured by Elixirgen Scientific, Inc.) were used.

In Table 2 below, "Suppression of drying of liquid pool" indicates the presence or absence and the kind of the drying-suppressing step for the liquid pools arranged on the substrate, and "Maintenance of shape of liquid pool" indicates whether or not the shape of the liquid pool was maintained after being left to stand at 37° C. for 60 minutes. Other items are the same as those shown in Table 1 above. The evaluation criteria for "Maintenance of shape of liquid pool" were as follows.

+: The shape of the liquid pool was maintained.

−: 80% or more of the liquid pool dried, and cell death was observed.

TABLE 2

|  | Reference Example 1 | Reference Example 2 | Reference Example 3 | Reference Example 4 |
|---|---|---|---|---|
| Diameter of Liquid pool (μm) | 400 | 400 | 400 | 400 |
| Cell density (cells/cm$^2$) | $8 \times 10^4$ | $2 \times 10^5$ | $8 \times 10^4$ | $2 \times 10^5$ |
| Number of cells (cells) | 100 | 320 | 100 | 320 |
| Inner diameter/outer diameter of non-adhesive portion (μm) | 300/600 | 300/600 | 300/600 | 300/600 |
| Diameter of adhesive portion (μm) | 400 | 400 | 400 | 400 |
| Cell arrangement method | IJ | IJ | IJ | IJ |
| Drying suppression of liquid pool | Oil | Oil | Not used | Not used |
| Initial arrangement of cells | + | + | + | + |
| Fixation of cells | + | + | − | − |
| Maintenance of shape of liquid pool | + | + | − | − |

The present invention includes the following aspects.

[1] A manufacturing method for a substrate on which nerve cells are arranged, the method including a step of forming one or a plurality of liquid pools by arranging a plurality of liquid droplets containing nerve cells on a substrate using an inkjet method, to form one or a plurality of liquid pools, where substrate has a region in which a cell adhesive material is arranged and a region in which a cell non-adhesive material is arranged; and a step of incubating the liquid pool until the nerve cells to sediment and temporarily adhere onto the substrate to form a cell aggregate, in which the diameter per one liquid pool is 500 μm or less, and the density of nerve cells per one liquid pool is $10^5$ cells/cm$^2$ or more.

[2] The manufacturing method according to [1], in which one liquid pool contains 7 to 10,000 nerve cells.

[3] The manufacturing method according to [1] or [2], in which one liquid droplet contains 1 to 50 nerve cells.

[4] The manufacturing method according to any one of [1] to [3], in which each liquid droplet is arranged to be in contact with the cell adhesive material.

[5] The manufacturing method according to any one of [1] to [4], further including a step of suppressing evaporation of a liquid in the liquid pool.

[6] The manufacturing method according to any one of [1] to [5], further including a step of supplying a medium to the substrate on which the cell aggregate is formed.

[7] The manufacturing method according to [6], further including a step of functionally binding at least two cell aggregates by incubating the substrate to which the medium has been supplied, in which a plurality of the liquid pools are formed in the step of forming the liquid pool, and a plurality of the cell aggregates are formed in the step of incubating.

[8] The manufacturing method according to any one of [1] to [7], in which the substrate has a region in which the cell non-adhesive material is arranged and a region in which the cell non-adhesive material is not arranged, the region in which the cell non-adhesive material is not arranged has a linear shape, and a width of the linear shape is 100 μM or less.

[9] The manufacturing method according to any one of [1] to [8], in which the substrate has a porous structure.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

EXPLANATION OF REFERENCES

10 . . . Liquid droplet ejection head
11, 970 . . . Cell ink
12, 25 . . . Liquid chamber
13, 28 . . . Membrane
14, 26 . . . Driving unit
15 . . . Nozzle
16, 27 . . . Vibration application portion
17, 24 . . . Atmospheric opening portion
21, 22, 23 . . . Inkjet head
31 . . . Stage portion
400, 500, 600, 700 . . . Liquid droplet-arranging device
910 . . . Flat plate member
920 . . . Porous member
930 . . . Cell culture carrier
940 . . . First solution
950 . . . Second solution
960 . . . Cell non-adhesive material
980 . . . Cells
Pj . . . Ejection waveform
Ps . . . Vibration isolation waveform.

What is claimed is:

1. A manufacturing method, the method comprising:
a step of forming one or a plurality of liquid pools by ejecting a plurality of liquid droplets comprising nerve cells from an inkjet head onto a substrate, to form one or a plurality of liquid pools, wherein the substrate has a region in which a cell adhesive material is arranged and a region in which a cell non-adhesive material is arranged; and
a step of incubating the liquid pool until the nerve cells in the liquid pool sediment and temporarily adhere onto the substrate to form a cell aggregate,
wherein the diameter per one liquid pool is 400 μm or less, and
the density of nerve cells per one liquid pool is $10^5$ cells/cm$^2$ or more.

2. The manufacturing method according to claim 1, wherein one liquid pool contains 7 to 10,000 nerve cells.

3. The manufacturing method according to claim 1, wherein one liquid droplet contains 1 to 50 nerve cells.

4. The manufacturing method according to claim 1, wherein each liquid droplet is arranged to be in contact with the cell adhesive material.

5. The manufacturing method according to claim 4, wherein each liquid droplet is arranged to be in contact with the cell adhesive material by a liquid-droplet-arranging device including a plate portion and an inkjet head.

6. The manufacturing method according to claim 1, further comprising a step of suppressing evaporation of a liquid in the liquid pool.

7. The manufacturing method according to claim 1, further comprising a step of supplying a medium to the substrate on which the cell aggregate is formed.

8. The manufacturing method according to claim 7, further comprising:
- a step of functionally binding at least two cell aggregates by incubating the substrate to which the medium has been supplied,
- wherein a plurality of the liquid pools are formed in the step of forming the liquid pool, and a plurality of the cell aggregates are formed in the step of incubating.

9. The manufacturing method according to claim 1, wherein the substrate has a region in which the cell non-adhesive material is arranged and a region in which the cell non-adhesive material is not arranged,
- the region in which the cell non-adhesive material is not arranged has a linear shape, and
- a width of the linear shape is 100 μm or less.

10. The manufacturing method according to claim 1, wherein the substrate has a porous structure.

11. The manufacturing method according to claim 1, wherein the diameter per one liquid pool is 300 μm or less.

12. The manufacturing method according to claim 1, wherein the diameter per one liquid pool is 200 μm or less.

13. A substrate, comprising nerve cells, and formed by the method according to claim 1.

14. The manufacturing method according to claim 1, wherein the inkjet method comprises a piezo method.

15. The manufacturing method according to claim 1, wherein one liquid pool contains 7 to 100 nerve cells.

16. The manufacturing method according to claim 1, wherein the cell non-adhesive material comprises a polyethylene glycol.

17. The manufacturing method according to claim 1, wherein the cell adhesive material comprises a protein.

18. The manufacturing method according to claim 1, wherein the one or a plurality of liquid pools comprises a cell-drying inhibitor.

19. The manufacturing method according to claim 1, wherein the cell adhesion material is arranged in a circle form and the cell non-adhesive material is arranged in a pattern to surround the cell adhesive material and comprises a hydrogel formed from Tetra-PEG-SH and Tetra-PEG-maleimide.

* * * * *